US007442377B2

(12) United States Patent
Steinman et al.

(10) Patent No.: US 7,442,377 B2
(45) Date of Patent: Oct. 28, 2008

(54) PROTECTIVE ANTIGEN OF EPSTEIN BARR VIRUS

(75) Inventors: Ralph M. Steinman, Westport, CT (US); Christan Muenz, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 11/359,868

(22) Filed: Feb. 21, 2006

(65) Prior Publication Data

US 2006/0188520 A1    Aug. 24, 2006

Related U.S. Application Data

(63) Continuation of application No. 10/049,316, filed as application No. PCT/US00/22106 on Aug. 10, 2000, now Pat. No. 7,005,131.

(60) Provisional application No. 60/148,971, filed on Aug. 13, 1999.

(51) Int. Cl.
*A61K 39/285* (2006.01)
*A61K 48/00* (2006.01)
*A61K 31/7105* (2006.01)
*A61K 31/7088* (2006.01)

(52) U.S. Cl. .................... 424/199.1; 424/93.21; 514/44

(58) Field of Classification Search .............. 424/229.1; 435/325, 4, 5; 530/389.6
See application file for complete search history.

(56) References Cited

U.S. PATENT DOCUMENTS 5,851,756 A    12/1998   Steinman et al.
6,994,851 B1 *  2/2006   Kundig et al. ............. 424/93.7

FOREIGN PATENT DOCUMENTS

CA       2180193      12/1996
WO       WO-96/02563   2/1996
WO       WO-97/24447   7/1997

OTHER PUBLICATIONS

Mukherjee et al., "Murine Cytotoxic T Lymphocytes Recognize an Epitope in an EBNA-1 Fragment, but Fail to Lyse EBNA-1-expressing Mouse Cells," J. Exp. Med., vol. 187, No. 3. pp. 445-450 (1998).*
Heller et al., "Virus-specific CD4+T cells: ready for direct attack," The Journal of Experimental Medicine, vol. 203, No. 4, pp. 805-807 (2006).*
Sample et al., "Nucleotide sequences of mRNAs encoding Epstein-Barr virus nuclear proteins: A probably transcriptional initiation site," Proc. Natl. Acad. Sci. vol. 83, pp. 5096-5100 (1986).*
Morrow et al (Current Topics in Microbiology & Immunology 236:255-273, 1999).*
Wong, C. et al., "Induction of Primary, Human Antigen-Specific Cytoxic T Lymphocytes In Vitro Using Dendritic Cells Pulsed with Peptides" (1998) Journal of Immunotherapy, 21(1):32-40.

Romani, et al., "Proliferating Dendritic Cell Progenitors in Human Blood" (1994) J Exp. Med. vol. 180: 83-93.
O'Doherty, et al. "Dendritic Cells Freshly Isolated from Human Blood Express CD4 and Mature Into Typical .Immunostimulatory Dendritic Cells After Culture in Monocyte-condition Medium", J. Exp. Med., vol. 178, Sep. 1993, pp. 1067-1078.
Rickinson AB and Kieff E., "Epstein-Barr Virus" In: Fields Virology, 3d Ed. 1996 pp. 2397-2448.
Blake, et al., Immunity, 7:791-802, 1997.
Chen, et al., J. Gen. Virol., 80:447-455, 1999.
Gutierrez, et al., J. Gen. Virol., 78:1663-70, 1997.
Inaba, et al., J. Exp. Med., 188:2163-73, 1998.
Khanna, et al., Eur. J. Immunol., 28:451-458, 1998.
Lee, et al., Eur. J. Immunol., 26:1875-83, 1996.
Levitskaya, et al., Nature, 375 685-688, 1995.
Rickinson and Moss, Ann. Rev. Immunol., 15:405-31, 1997.
Steinman, Exper. Hematol., 24:859-862, 1996.
Steven, et al., J. Exp. Med., 184:1801-13, 1996.
Yates, et al., Nature, 313:815, 1985.
Thomson, S.A. et al., "Targeting a Polyepitope Protein Incorporating a Multiple Class II-Restricted Viral Epitopes to the Secretory/Endocytic Pathway Facilitates Immune Recognition bu CD4 + Cytoxic T Lymphocytes: A Novel Approach to Vaccine Design", Journal of Virology, vol. 72, No. 3, Mar. 1998, pp. 2246-2252.
Khanna, R. et al., "Targeting Epstein-Barr Virus Nuclear Antigen 1 (EBNA1) Through The Class II Pathway Restores Immune Recognition by EBNA1 --Specific Cytoxic T Lymphocytes: Evidence for HLA-DM-Independent Processing", International Immunology, vol. 9, No. 10, Oct. 1997, pp. 1537-1543.
Murray, R.J. et al., "Identification of Target Antigens for the Human Cytoxic T Cell Response to Epstein-Barr Virus (EBV): Implications for the Immune Control of EBV-Positive Malignancies", Journal of Experimental Medicine, vol. 176, No. 1, Jul. 1, 1992, pp. 157-168.
Di Nicola, M. et al., "Gene Transfer into Human Dendritic Antigen-Presenting Cells by Vaccinia Virus and Adenovirus Vectors", Cancer Gene Therapy, vol. 5, No. 6, Nov. 1998, pp. 350-356.
Khanna, R. et al., "Vaccine Strategies Against Epstein-Barr Virus-Associated Diseases:Lessons from Studies on Cytotoxic T-Cell-Mediated Immune Regulation", Immunological Reviews, vol. 170, Aug. 1999, pp. 49-64.

(Continued)

*Primary Examiner*—Mary E Mosher
(74) *Attorney, Agent, or Firm*—Darby & Darby P.C.

(57) ABSTRACT

The present invention relates to the identification of a subunit vaccine to prevent or treat infection of Epstein Barr Virus. In particular, EBNA-1 was identified as a vaccine antigen. In a specific embodiment, a purified protein corresponding to EBNA-1 elicited a strong CD4+ T cell response. The responsive CD4+ T cell are primarily $T_H1$ in function. EBNA-1 is an attractive candidate for a protective vaccine against EBV, and for immunotherapy of EBV infection and neoplasms, particularly with dendritic cells charged with EBNA-1.

6 Claims, 24 Drawing Sheets

OTHER PUBLICATIONS

Tarte, K. et al., "Dendritic Cell-Based Vaccine: A Promising Approach for Cancer Immunotherapy", Leukemia, vol. 13, No. 5, May 1999, pp. 653-663.

Munz, C. et al., "Human CD4(+) T Lymphocites Consistently Respond to the Latent epstein-barr Virus Nuclear Antigen EBNA1", Journal of Experimental Medicine, vol. 107, No. 10, May 15, 2000, pp. 1649-1660.

Bickham, K. et al., "EBNA1-Specific CD4 + T Cells in Healthy Carriers of Epstein-Barr Virus are Primarily TH1 in Function", Journal of Clinical Investigation, vol. 107, No. 1, Jan. 2001, pp. 121-130.

* cited by examiner

CD2⁺PBMC

CD8⁻CD2⁺PBMC

CD4⁻CD2⁺PBMC

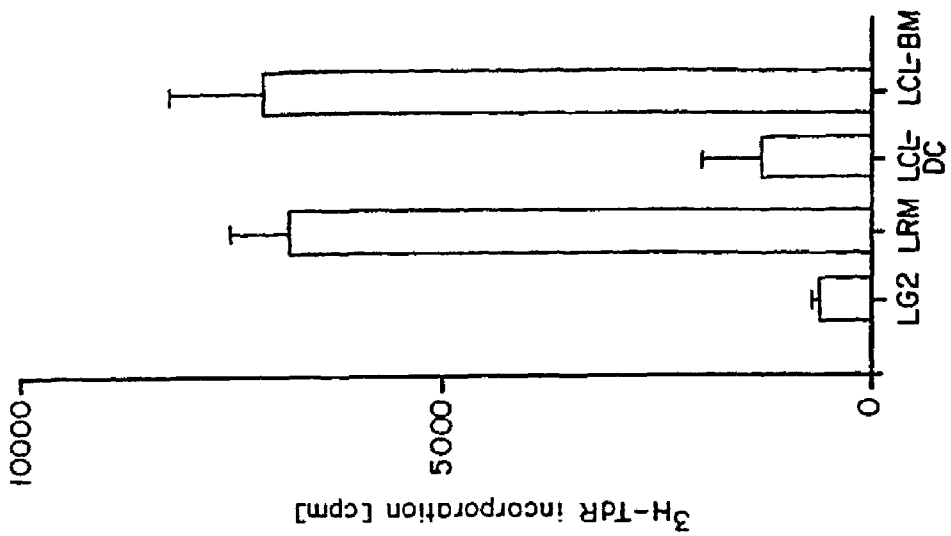
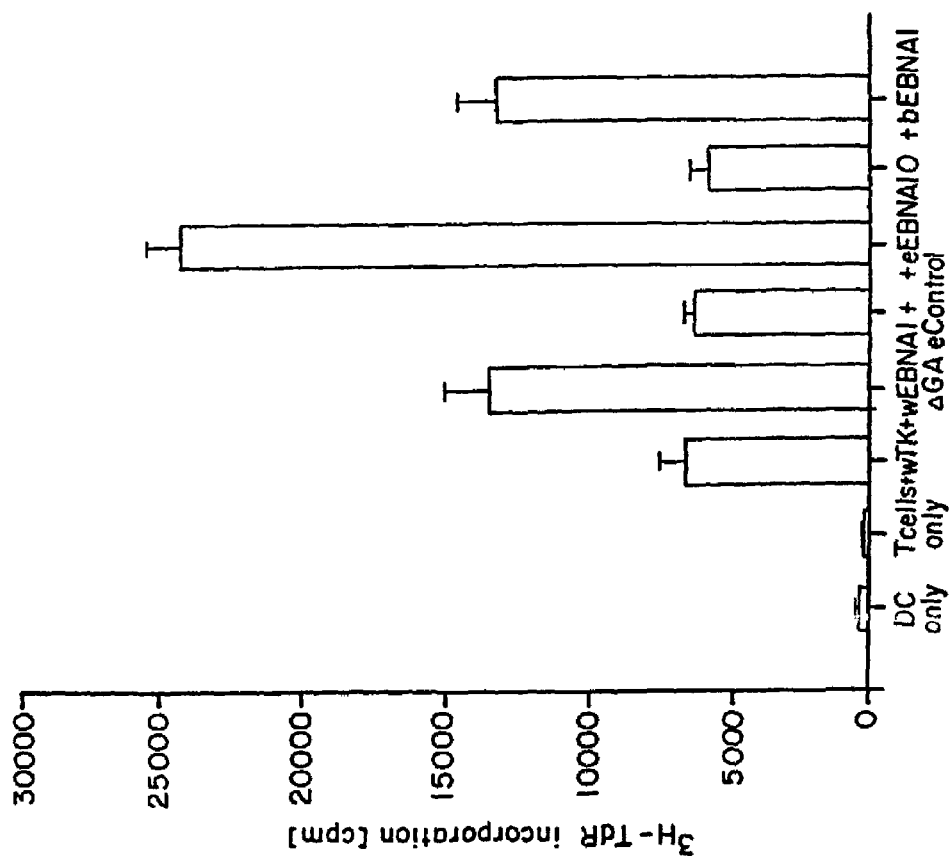

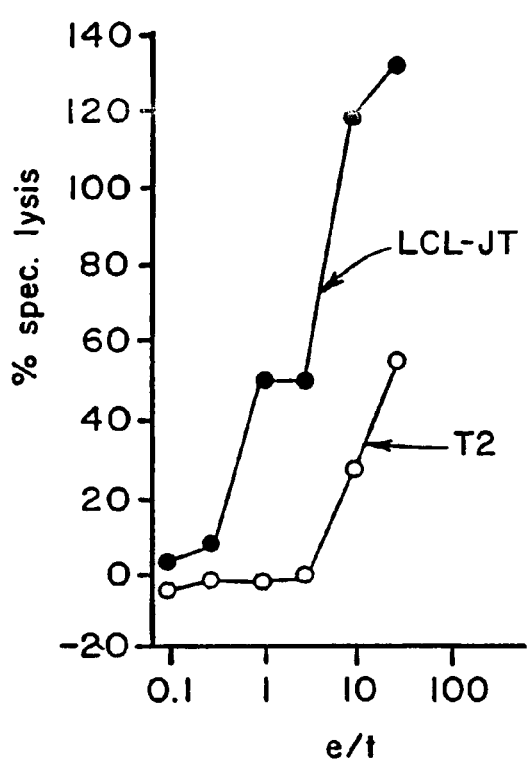
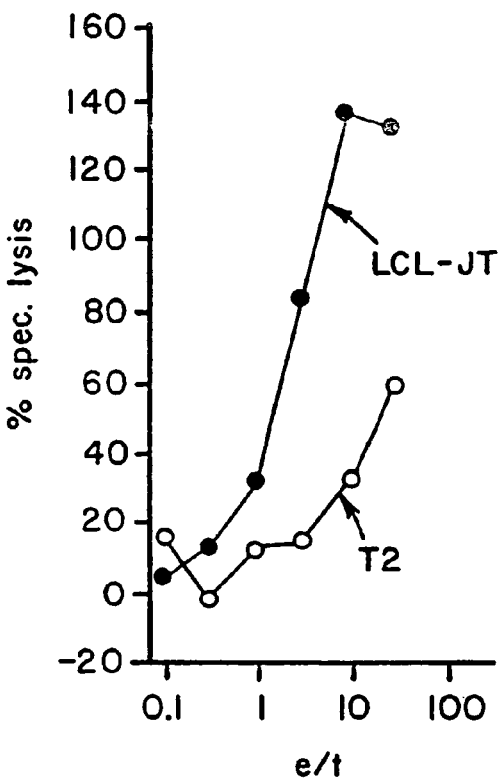
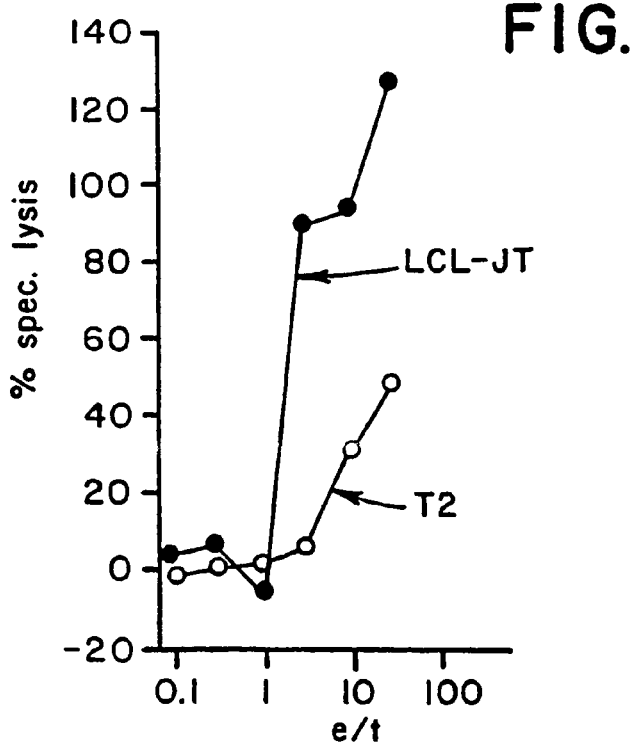

LCL targets:
● LCL-JT
○ LCL-JT + L243
▼ T2

DC targets:
- eControl
- eEBNA1
- bEBNA1
- LCL-JT

FIG. 8A

PROTECTIVE ANTIGEN OF EPSTEIN BARR VIRUS

This application is a continuation of U.S. patent application Ser. No. 10/049,316, filed Feb. 8, 2002 (now U.S. Pat. No. 7,005,131), which is a U.S. national phase application under 35 U.S.C. §371 based on international Application No. PCT/US00/22106, filed Aug. 10, 2000, which claims the benefit of priority of U.S. provisional Application No. 60/148,971, filed Aug. 13, 1999. The entire disclosures of the prior applications are incorporated herein by reference. The international application was published in the English language on Feb. 22, 2001 under Publication No. WO 01/12215.

This work was supported in part by National Institutes of Health Grant No. K12-HD00850 and NIAID grants AI40045 and AI40874. Accordingly, the United States government may have certain rights in the invention.

FIELD OF THE INVENTION

The present invention relates to the identification of a vaccine to prevent or treat Epstein Barr Virus infection. In particular, the EBNA-1 antigen was identified as a vaccine antigen. Exposure to EBNA-1 can be exploited for its immunoprotective effect in humans and in animals.

BACKGROUND OF THE INVENTION

EBV is a human gamma herpesvirus with a tropism for B lymphocytes (Kieff and Liebowitz, in Virology, eds. Fields, B. N., Knipe, D. M. et al., p. 1889-1919, Raven Press, Ltd.: New York, 1990). Greater than 95% of the adult population carry EBV as a lifelong asymptomatic infection. However EBV has strong growth transforming capacities (Klein, Cell, 77:791-3, 1994), transforming B cells and presumably other cell types in a spectrum of EBV-associated malignancies including Hodgkin's lymphoma, nasopharyngeal carcinoma, T cell lymphoma, gastric carcinoma, and uterine leiomyosarcoma.

Three specific EBV genes are critical for tumorigenesis and induce cell proliferation as well as resistance to apoptosis (Gregory, et al., Nature, 349:612-4, 1991). EBNA-1 links as a dimer the viral origin of replication and the host cell DNA and ensures episomal replication during B cell growth (Bochkarev, et al., Cell, 84:791-800; Shah, et al., J. Virol., 66:3355-62, 1992). The two latent membrane proteins (LMP) have different roles. The C-terminal part of LMP1 can act as a direct oncogene (Wang, et al., Cell, 43:831-40, 1985) by mimicking CD40-mediated B cell activation (Busch and Bishop, J. Immunol., 162:2555-2561, 1999). Thus, LMP1 engages signaling proteins for the tumor necrosis factor receptor family (Mosialos, et al., Cell, 80:389-99, 1995) and protects against apoptosis by induction of bcl-2 (Henderson, et al., Cell, 65:1107-15, 1991). LMP2 mimics B cell receptor signaling by constitutively engaging syk and lyn, protein tyrosine kinases (Caldwell, et al., Immunity, 9:405-11, 1998). These three proteins appear to be the exclusive EBV genes that are expressed in most EBV-induced tumors (Miller, et al., in Virology, eds. Fields, B. N., Knipe, D. M. et al., p. 1921-1958, Raven Press, Ltd.: New York, 1990). In Burkitt's lymphoma, only EBNA-1 is required for EBV persistence, since transformation is achieved by an additional mechanism involving c-myc uncoupling through chromosomal translocation (Klein, supra).

The reason why most carriers of EBV avoid transformation remains to be elucidated. Immunity to EBNA-1 a priori could provide resistance to transformed cells, but it has proven difficult to detect specific T cell responses to this essential protein for EBV persistence. In fact, EBNA-1 blocks its own processing for MHC class I presentation (Blake, et al., Immunity, 7:791-802, 1997). This has been attributed to a deficit in proteasomal processing, caused by the N-terminal GA repeat domain (Levitskaya, et al., Nature, 375:68508, 1995). A similar GA stretch prevents IκBα degradation by the proteasome (Sharipo, et al., Nat Med., 4:939-44, 1998). Other EBV latency gene products are the focus of a strong MHC class I restricted CTL response, especially EBNA3A, 3B, and 3C (Steven, et al., J. Exp. Med., 184:1801-13, 1996). However, the EBNA3 proteins are not expressed in most of the EBV-associated tumors mentioned above, and instead are expressed in cultured transformed lines (B-LCL) and lymphoproliferative syndromes in immunosuppressed patients. $CD8^+$ CTL responses to tumor-associated LMP1 (Khanna, et al., Eur. J. Immunol., 28:451-8, 1998) and LMP2 (Lee, et al., Eur. J. Immunol., 26:1875-83, 1996) proteins have been detected, but only occasionally.

It is becoming apparent that the development and persistence of effective $CD8^+$ CTLs are dependent on $CD4^+$ T cell help (Kalams and Walker, J. Exp. Med., 188:2199-204, 1998). Recognition of EBV products by $CD4^+$ T cells has not been investigated in the same detail as the $CD8^+$ response (Rickinson and Moss, Ann. Rev. Immunol., 15:405-31, 1997). Dendritic cells (DCs) are potent antigen presenting cells for $CD4^+$ and $CD8^+$ T cell immunity (Banchereau and Steinman, Nature, 392:245-52, 1998).

Thus, the efforts to identify a protective antigen in Epstein Barr Virus have been inconclusive, and it is unknown whether a single or multiple antigens are necessary to provide complete protection from infection. Furthermore, EBNA-1 is not believed to elicit protective immunity to the virus.

SUMMARY OF THE INVENTION

The present invention advantageously identifies an immuno-protective antigen from EBV, which can be used in vaccine and immunotherapy approaches to preventing or treating EBV infection in humans.

In on embodiment, the invention provides a vaccine comprising an immunogenic EBNA-1 polypeptide and an adjuvant acceptable for use in a human. The immunogenic EBNA-1 polypeptide can be a fusion protein of EBNA-1 and a heterologous amino acid sequence.

In another embodiment, the invention provides an expression vector for expression in humans comprising a sequence encoding an immunogenic EBNA-1 polypeptide, operably associated with an expression control sequence. A preferred vector of the invention preferentially targets dendritic cells. The invention specifically contemplates viral vectors, such as a vaccinia virus vector, Fowl pox, AV-pox, and modified vaccinia Ankara (MVA) virus.

Also provided are methods for protecting a subject from infection by Epstein Barr Virus. One such method comprises delivering an immunologically effective amount of an immunogenic EBNA-1 polypeptide to the subject. Another such method comprises delivering an immuno-protective amount of the expression vector of the invention to the subject. Preferably such an expression vector targets dendritic cells in vivo. These methods are useful to prevent or treat an EBV-associated neoplasm, such as (but not limited to) nasopharyngeal carcinoma.

The present invention is further explained and exemplified in the following Detailed Description and Example.

BRIEF DESCRIPTION OF THE DRAWINGS

FIGS. 3A and 3B. Proliferative responses of the CM171198 cell line to various EBNA-1 expressing targets. A: DCs (DC only) and T cells (T cells only) show low background proliferation. When mixed (0) there is some proliferation that can be increased upon infection with a recombinant vaccinia virus construct expressing EBNA-1 (vvEBNA-1ΔGA) but not vector alone (vvTK−). External loading of DCs with recombinant EBNA-1 proteins from E. coli (eEBNA-1) and baculovirus/insect cell (bEBNA-1) expression systems also augments the proliferation, while there is no reactivity against an E. coli derived control protein (eControl). B: B-LCL sharing the HLA-DR4 allele with the CM171198 cell line induce proliferation (LRM and LCL-BM) while HLA-DR4 mismatched B-LCL do not (LG2 and LCL-DC).

FIGS. 6A and 6B. Specificity of CD4+ CTL clones. B-LCL were generated from samples of 2 leukocyte concentrates. Cryopreserved CD8−CD2+PBMC were then stimulated for 2 weeks with these autologous B-LCL under limiting dilution. Afterwards the wells were split and tested in $^{51}$Cr release assays against vvEBNA-1ΔGA (open bar) or vvTK− (dark solid bar) infected DCs as well as autologous B-LCL (gray solid bar) and LCL721.221 (second open bar), a HLA class I− NK target. 11 clones recognizing EBNA-1 epitopes on EBV transformed B cells are shown. They were derived from 2 leukocyte concentrates in 2 independent experiments (A,B).

Figure 1A:
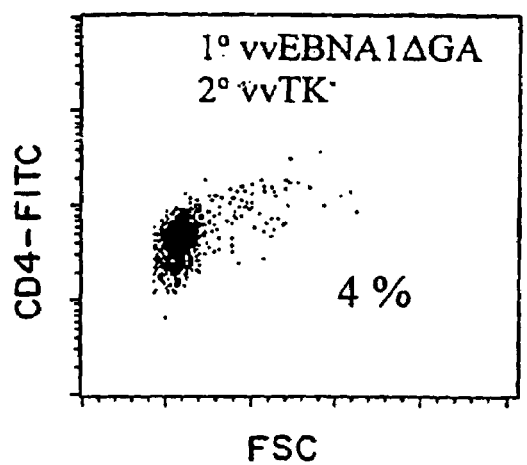
FIGS. 1A, 1B, 1C, 1D, 1E, and 1F. EBNA-1 is preferentially recognized by CD4+ T cells. Blast formation by CD4+ T cells (CD4-FITC) was monitored by flow cytometry. The forward scatter indicates the size of the cells. Cultures of CD2+CD8− T cells, stimulated with autologous DC infected with vaccinia virus constructs, were analyzed. A. Culture stimulated with vvEBNA-1ΔGA infected DCs and restimulated with vvTK− infected DCs. B. Blasting of a culture stimulated with vvEBNA-1ΔGA infected DCs and restimulated with vvEBNA-1ΔGA infected DCs. C. Culture stimulated with vvEBNA3A infected DCs and restimulated with vvTK− infected DCs. D. T cells were stimulated and restimulated with vvEBNA3A infected DCs. E. Culture stimulated and restimulated with vvTK− infected DCs to evaluate the background of vaccinia stimulation. F. CD2+CD8− T cells responding to influenza virus infected DCs as positive control. All cultures were prepared from the same donor (No. 5 in Table 1). Percent of blasted subpopulations (arrows) are indicated.
Figure 1B:
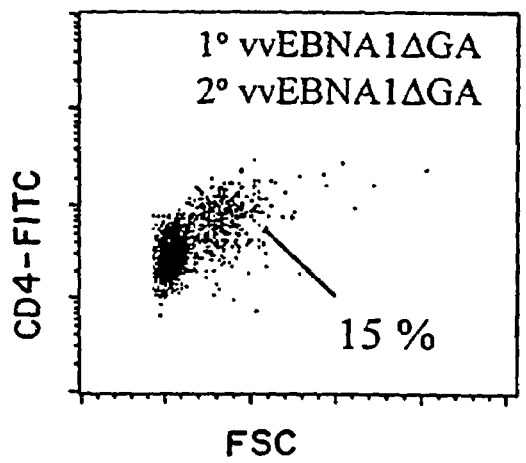
Figure 1C:
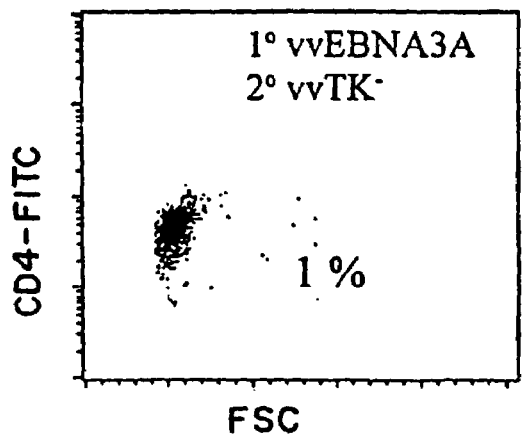
Figure 1D:
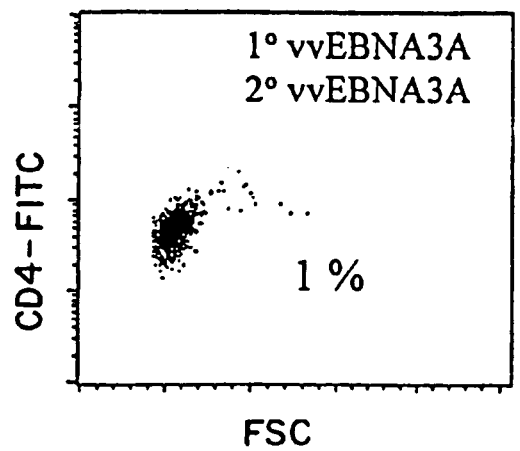

Cell lines were isolated from PBMCs stimulated with vvEBNA-1ΔGA-infected DCs for either 7 hours (IFNγ) or 18 hours (IL-4). The cells were then positively selected based on the secretion of IFNγ or IL-4. EBNA-1-specific IFNγ and IL-4 producing cells were isolated from 6/6 donors and 3/6 donors, respectively. These cells were expanded with weekly restimulations of irradiated vvEBNA-1ΔGA-infected DCs alternating with DCs pulsed with a rEBNA-1 protein. A, B. Cells were restimulated with vvEBNA-1ΔGA-infected (open bar) or vvTK⁻ infected (solid bar) DCs and tested for either IFNγ or IL-4 secretion after three weeks of expansion. The IFNγ-secreting cell line isolated from LD03 which is representative of all $T_H1$ cell lines is shown in panel A, and a representative EBNA-1-specific IL-4 secreting cell line from LD01 is illustrated in panel B. C, D. Cells were then tested for their ability to lyse vvEBNA-1ΔGA-infected DCs by $^{51}$Cr release assay. C. The results of the $^{51}$Cr release from LD03 cell line are shown with graded effector to target ratios and are representative of all six established IFNγ cell lines. D. Results shown are from a cell line established from LD01 and are representative of all IL-4-secreting cell lines isolated. E. CTL assay results at an effector to target ratio of 10:1 are shown for 5 IFNγ cell lines and 3 IL-4 lines for three sources of EBNA-1 antigen (vvEBNA-1ΔGA, rEBNA-1 or the physiologically expressed protein in BLCL) as compared to controls (vvTK, rPCNA control protein, T2 cells, respectively). Different symbols are representative of each cell line with $T_H1$ cell lines in white and $T_H^2$ cell lines in black. $T_H1$ and $T_H2$ cell lines isolated from the same donor share symbol shapes.

FIGS. 11A, 11B, 11C, 11D, and 11E. EBNA-1-specific antibodies are predominantly IgG1. Values are shown for each donor, with mean values indicated by black bars. The background levels in the absence of antigen (A) for each IgG subclass were subtracted from the results with the microbial proteins. IgG subclass distribution of antibodies specific to a rEBNA-1 protein are shown (B), as are the IgG subclass distribution to tetanus toxoid (C), candida (D) and mumps (E).

DETAILED DESCRIPTION OF THE INVENTION

The present invention is based, in part on unexpected discoveries concerning a protective antigen of Epstein Barr Virus (EBV). In most EBV seropositive adults, strong CD8⁺ cytotoxic T lymphocytes (CTL) responses have been demonstrated (Murray, et al., J. Exp. Med., 1992, 176:157-168). However, these are preferentially directed toward the nuclear antigens, EBNA3A, 3B and 3C (Kieff, E., Epstein-Barr Virus and Its Replication. In Fields Virology. B. N. Fields, D. M. Knipe, and P. M. Howley, editors. 1996, Lippincott-Raven Publishers, Philadelphia. 2343-2396; Khanna, et al. J. Exp. Med., 1992, 176:169-176), which are not expressed in many EBV-associated malignancies. EBV-transformed cells exhibit one of three latency phenotypes distinguished from each other by the panel of expressed EBV antigens (Murray, et al., 1992, supra). In latency I, e.g., Burkitt's lymphoma, EBNA-1 alone is expressed. In latency II, exemplified by Hodgkin's lymphoma, LMP1 and LMP2 as well as EBNA-1 are expressed. Only in latency m immunoblastic lymphomas are the highly immunogenic EBNA3 genes expressed. Therefore, many EBV-associated malignancies do not seem to provide good targets for the human CD8⁺ T cell response to EBV latency gene products.

The evidence in the present invention suggests that, unexpectedly, the Epstein-Barr virus (EBV) encoded nuclear antigen (EBNA-1) is an effective antigen for developing an EBV vaccine, particularly an anti-tumor vaccine. EBNA-1 immunity greatly reduces viral replication because this antigen is crucial for the persistence of the EBV episome in replicating EBV-transformed human B cells (Yates, et al., Nature, 313: 812-5, 1985). Therefore, all EBV-induced tumors express this foreign antigen. However, EBNA-1 protein is invisible to CD8⁺ cytotoxic T lymphocytes (CTLs). The gly-ala repeat domain prevents proteasome dependent processing and thus presentation on MHC class I (Levitskaya, et al., supra). It has now been found that CD4⁺ T cells from most individuals do respond to EBNA-1. In fact, among EBV latent antigens that stimulate CD4⁺ cells, EBNA-1 is preferentially recognized. Recognition can occur via endogenous and exogenous processing of EBNA-1 onto MHC class II molecules of dendritic cells (DCs). The CD4⁺ response includes direct cytolysis of transformed B lymphocyte cell lines (B-LCL). Therefore, the immune system can recognize the EBNA-1 protein that is crucial for EBV persistence.

The type of CD4⁺ T cell also influences the response (reviewed in O'Garra, and Murphy, Curr. Opin. Immunol., 1994, 6:458-66. 20). $T_H1$ CD4⁺ cells secrete IFNγ and help in the development of cellular immunity, including the activation of macrophages. $T_H2$ CD4⁺ cells secrete IL-4 and IL-5, thereby stimulating eosinophils and antibody production. The expression of specific chemokine receptors on the $T_H1$ cells results in the migration of the $T_H1$ cells to the normal cites of inflammation. $T_H2$ cells migrate to cites more closely associated with allergic responses. CD4⁺ T cells also can kill targets (reviewed in Hahn, et al., Immunol Rev., 1995., 146:57-79), primarily through Fas-FasL interactions. Cytotoxicity mainly has been found with $T_H1$ CD4⁺ cells (Erb, et al., Cell Immunol., 1991, 135:232-44; Erb, et al., J. Immunol., 1990, 144: 790-795; Del Prete, et al., J. Exp. Med., 1991, 174:809-13; Nishimura, et al., J. Exp. Med., 1999, 190:617-628.), but a limited number of cytotoxic $T_H2$ CD4⁺ clones have been reported (Lancki, et al., J. Immunol., 1991, 146:3242-9).

Evidence suggests that the EBNA-1-specific, CD4⁺ T cell response in cells that are directly isolated from blood is predominantly a $T_H1$ response. Furthermore, the isotype of the EBNA-1 antibody response is skewed to the IgG1 subclass, reflecting $T_H1$ polarization in vivo. This result has important implications for a therapeutic vaccine for EBNA-1 based on the emerging evidence that $T_H1$ cells are important for resistance to viruses and tumors, and thus are key to long term immunity.

Immunotherapy of EBV with EBNA-1 provides significant advantages of safety and efficacy. Subunit vaccines ensure the greatest degree of safety because there is no opportunity for infection by the pathogen. This is always of some concern when immunizing with killed or attenuated virus. Furthermore, a single component minimizes adverse side effects, such as anaphylaxis or antigen cross reactivity, that may result from an unrelated antigen in a whole virus vaccine. Immunotherapy with dendritic cells charged with EBNA-1 has substantial therapeutic potential. Furthermore, because EBNA-1 is involved in EBV infection and tumorigenesis, it will elicit the most protective immune response to prevent or treat EBV infection and associated diseases or disorders. Another alternative vaccine approach is to define the DR-specific peptides in the EBNA-1 protein. Pulsing dendritic cells with these peptides, and then immunizing subjects with the pulsed dendritic cells would establish the protective effect of the vaccine strategy.

The term "vaccine" refers to a composition (protein or vector; the latter may also be loosely termed a "DNA vaccine", although RNA vectors can be used as well) that can be used to elicit protective immunity in a recipient. It should be noted that to be effective, a vaccine of the invention can elicit immunity in a portion of the population, as some individuals may fail to mount a robust or protective immune response, or, in some cases, any immune response. This inability may stem from the individual's genetic background or because of an immunodeficiency condition (either acquired or congenital) or immunosuppression (e.g., treatment with immunosuppressive drugs to prevent organ rejection or suppress an autoimmune condition). Efficacy can be established in animal models.

The term "immunotherapy" refers to a treatment regimen based on activation of a pathogen-specific immune response. A vaccine can be one form of immunotherapy. Charging dendritic cells with EBNA-1 antigen, preferably with a stimulatory cytokine such as GM-CSF or Flt3 ligand ex vivo (followed by transplantation into the subject) or in vivo is also a form of immunotherapy.

The term "protect" is used herein to mean prevent or treat, or both, as appropriate, an EBV infection in a subject. Thus, prophylactic administration of the vaccine can protect the recipient subject from EBV infection, e.g., to prevent infectious mononucleosis or lymphoproliferative diseases. Therapeutic administration of the vaccine or immunotherapy can protect the recipient from EBV-infection-mediated pathogenesis, e.g., to treat a disease or disorder such as an EBV-associated neoplasm, EBV-associated neoplasms include Hodgkin's lymphoma, endemic Burkitt's lymphoma, nasopharyngeal carcinoma, T cell lymphoma, gastric carcinoma, and uterine leiomyosarcoma.

The term "subject" as used herein refers to an animal that supports EBV. In particular, the term refers to a human.

The term "vector for expression in humans" as used herein means that the vector at least includes a promoter that is effective in human cells, and preferably that the vector is safe and effective in humans. Such a vector will, for example, omit extraneous genes not involved in developing immunity. If it is a viral vector, it will omit regions that permit replication and development of a robust infection, and will be engineered to avoid development of replication competence in vivo. Such vectors are preferably safe for use in humans; in a more preferred embodiment, the vector is approved by a government regulatory agency (such as the Food and Drug Administration) for clinical testing or use in humans. Specific vectors are described in greater detail below.

An "adjuvant" is a molecule or composition that potentiates the immune response to an immunogen. An adjuvant is "acceptable for use in a human" when it is pharmaceutically acceptable, as defined below. Examples of adjuvants are provided below.

The Immuno-Protective Antigen of Epstein Barr Virus

The present invention provides an immunoprotective antigen of Epstein Barr Virus, a protective or therapeutic protein or DNA vaccine, and immunotherapy using EBNA-1 charged dendritic cells to prevent or treat EBV infection. The immunoprotective antigen is an immunogenic EBNA-1 polypeptide. As discussed in greater detail below, an EBNA-1 polypeptide can be an EBNA-1 protein, a fusion protein comprising an amino acid sequence, or a fragment of EBNA-1 that includes the immunoprotective epitope.

The term "immunogenic EBNA-1-polypeptide" refers to the EBNA-1 protein, or a portion thereof, that is immunogenic and elicits a protective immune response when administered to an animal. Thus, an EBNA-1 immunoprotective antigen need not be the entire protein. The protective immune response generally involves cellular immunity at the CD4$^+$ T cell level.

The immunogenic polypeptide can comprise an immunoprotective EBNA-1 antigen from any strain of Epstein Barr Virus, or sequence variants of EBNA-1, as found in nasopharyngeal carcinoma and infected individuals (Chen et al., J. Gen. Virol., 80:447, 1999; Gutierrez et al., J. Gen. Virol., 78:1663, 1997).

As used herein, the term "immunogenic" means that the polypeptide is capable of eliciting a humoral or cellular immune response, and preferably both. An immunogenic polypeptide is also antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and preferably at least about 10, amino acids. An antigenic portion of a polypeptide, also called herein the epitope, can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

The term "carrier polypeptide" as used herein refers to a protein or immunogenic fragment thereof that can be conjugated or joined with the immunogenic EBNA-1 to enhance immunogenicity of the polypeptide. Examples of carrier proteins include, but are by no means limited to, keyhole limpet hemocyanin (KLY), albumin, cholera toxin (discussed in greater detail below), heat labile enterotoxin (LT), and the like. While chemical cross-linking of a peptide comprising the immuno-protective epitope of EBNA-1 with the carrier polypeptide can be used to prepare an immunogenic polypeptide, preferably the two components are prepared as a chimeric construct for expression as a fusion polypeptide.

In addition, chimeric fusion polypeptides of the immunogenic polypeptide with a purification handle, such as FLAG or GST (for immunopurification), or a HIS-tag (for Ni-chelation purification), are contemplated.

Where the full length recombinant EBNA-1 is used as the immunogenic polypeptide, preferably it is free from viral components, e.g., in distinction to vaccines comprising whole killed or attenuated virus. EBNA-1 polypeptide can be purified after recombinant expression, or it can be delivered by expression in situ, i.e., by expression from a vector (a DNA vaccine).

In addition, the present invention permits use of various mutants, sequence conservative variants, and functional conservative variants of EBNA-1, provided that all such variants retain the required immuno-protective effect.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein) expressed by a modified gene or DNA sequence. The term "variant" may also be used to indicate a modified or altered gene, DNA sequence, enzyme, cell, etc., i.e., any kind of mutant.

"Sequence-conservative variants" of a polynucleotide sequence are those in which a change of one or more nucleotides in a given codon position results in no alteration in the amino acid encoded at that position. Allelic variants can be sequence-conservative variants.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Some allelic variations result in functional-conservative variants, such that an amino acid substitution does not dramatically affect protein function. Similarly, homologous proteins can be function-conservative variants. Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck, et al., Cell 50:667, 1987). Such proteins (and their encoding genes) have sequence homology, as reflected by their sequence similarity, whether in terms of percent similarity or the presence of specific residues or motifs.

Accordingly, the term "sequence similarity" in all its grammatical forms refers to the degree of identity or correspondence between nucleic acid or amino acid sequences of proteins that may or may not share a common evolutionary origin (see Reeck, et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when a sufficient number of the nucleotides match over the defined length of the DNA sequences to differentiate the sequences from other sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when enough of the amino acids are identical or similar (functionally identical) over a defined length to differentiate the sequences from other sequences. Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

Furthermore, it should be noted that depending on the expression system employed, the expressed protein can differ from the predicted amino acid sequence encoded by a coding sequence. For example, a construct for expression of the immunogenic polypeptide can express a protein comprising a signal sequence, which may be cleaved or not during cellular processing. In addition, other proteolytic cleavages may occur during expression. If the polypeptide is expressed in eukaryotic cells, it may be glycosylated if it contains a glycosylation site. Other possible changes include N-methylation, and the like.

As used herein, the term "isolated" means that the referenced material is removed from its native environment, e.g., a cell. Thus, an isolated biological material can be free of some or all cellular components, i.e., components of the cells in which the native material occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including without limitation preparative solid phase chromatography, oligonucleotide hybridization, and triple helix chromatography), ultracentrifugation, and other means. Polypeptides and proteins can be purified by various methods including, without limitation, preparative disc-gel electrophoresis and isoelectric focusing; affinity, HPLC, reversed-phase HPLC, gel filtration or size exclusion, ion exchange and partition chromatography; precipitation and salting-out chromatography; extraction; and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, logarithmic terms used in biology, the term "about" can mean within an order of magnitude of a given value, and preferably within one-half an order of magnitude of the value.

Recombinant Expression Systems

The present invention contemplates various cloning and expression vectors for expression of the immunogenic polypeptides described herein. Such expression vectors can be used to transform cells in vitro to produce immunogenic polypeptides for protein vaccines, or in vivo to express the immunogenic polypeptide for a DNA vaccine.

The coding sequence for an immunogenic polypeptide may, and preferably does, include a signal sequence, which can be a heterologous signal sequence, e.g., for optimized signal sequence processing in a bacterial, yeast, insect, or mammalian cell. The term "signal sequence" is used herein to refer to the N-terminal, hydrophobic sequence found on most secreted proteins that identifies it for processing for secretion from the cell. Generally, the signal sequence is cleaved during processing. However, various constructs of the invention can include a partial signal sequence. It is not necessarily the case that the partial signal sequence is processed normally, or that it even provides for translocation during expression, e.g., to the bacterial periplasm.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Molecular Biology Definitions

A "nucleic acid molecule" (or alternatively "nucleic acid") refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. This term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The coding sequences herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

The term "gene", also called a "structural gene" means a DNA sequence that codes for or corresponds to a particular sequence of amino acids which comprise all or part of one or more proteins, and may or may not include regulatory DNA sequences, such as promoter sequences, which determine for example the conditions under which the gene is expressed.

The introduced gene or coding sequence may also be called a "cloned", "foreign", or "heterologous" gene or sequence, and may include regulatory or control sequences used by a cell's genetic machinery. The gene or sequence may include nonfunctional sequences or sequences with no known function.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. A host cell has been "transfected" by exogenous or heterologous DNA when such DNA has been introduced inside the cell. A cell has been "transformed" by exogenous or heterologous DNA when the transfected DNA is expressed and effects a function or phenotype on the cell in which it is expressed. The term "expression system" means a host cell transformed by a compatible expression vector and cultured under suitable conditions e.g. for the expression of a protein coded for by foreign DNA carried by the vector and introduced to the host cell.

Proteins and polypeptides can be made in the host cell by expression of recombinant DNA. As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell, e.g., the naturally occurring form (or forms) of the amino acid-based polymer. Generally, a DNA sequence having instructions for a particular protein or enzyme is "transcribed" into a corresponding sequence of RNA. The RNA sequence in turn is "translated" into the sequence of amino acids which form the protein or enzyme. An "amino acid sequence" is any chain of two or more amino acids.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively associated with" of transcriptional and translational (i.e., expression) control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular, or secreted. The term "intracellular" means something that is inside a cell. The term "extracellular" means something that is outside a cell, either in the cell membrane or secreted from the cell. A substance is "secreted" by a cell if it appears in significant measure in the external medium outside the cell, from somewhere on or inside the cell.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g., for the expression of a protein coded for by foreign DNA carried by the vector and introduced to the host cell. Expression systems include bacterial, insect, or mammalian host cells and vectors. Bacterial and insect cell expression is exemplified infra. Suitable mammalian cells include C12 cells, CHO cells, HeLa cells, 293 and 293T (human kidney cells), COS cells, mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is a such an element operatively associated with a different gene than the one it is operatively associated with in nature. In the context of the present invention, an gene is heterologous to the recombinant vector DNA in which it is inserted for cloning or expression, and it is heterologous to a host cell containing such a vector, in which it is expressed, e.g., a CHO cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). For hybrids of greater than 100 nucleotides in length, equations for calculating $T_m$ have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8). A minimum length for a hybridizable nucleic acid is at least about 10 nucleotides; preferably at least about 15 nucleotides; and more preferably the length is at least about 20 nucleotides.

Expression Vectors

A wide variety of host/expression vector combinations (i.e., expression systems) may be employed in expressing the immunogenic polypeptides of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, SV40 and pMal-C2, pET, pGEX (Smith, et al., Gene 67:31-40, 1988), pMB9 and their derivatives, plasmids such as RP4; gram positive vectors such as Strep. gardonii; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. Nos. 5,385,839 and 5,168,062), the SV40 early promoter region (Benoist and Chambon, Nature 290:304-310, 1981), the promoter contained in the 3' long terminal repeat of Rous sarcoma virus (Yamamoto, et al., Cell 22:787-797, 1980), the herpes thymidine kinase promoter (Wagner, et al., Proc. Natl. Acad. Sci. U.S.A. 78:1441-1445, 1981), the regulatory sequences of the metallothionein gene (Brinster, et al., Nature 296:39-42, 1982); prokaryotic expression vectors such as the b-lactamase promoter (Villa-Komaroff, et al., Proc. Natl. Acad. Sci. U.S.A. 75:3727-3731, 1978), or the tac promoter (DeBoer, et al., Proc. Natl. Acad. Sci. U.S.A. 80:21-25, 1983); see also "Useful proteins from recombinant bacteria" in Scientific American, 242:74-94, 1980; promoter elements from yeast or other fungi such as the Gal 4 promoter, the ADC (alcohol dehydrogenase) promoter, PGK (phosphoglycerol kinase) promoter, alkaline phosphatase promoter; and control regions that exhibit hematopoietic tissue specificity, in particular: immunoglobin gene control region, which is active in lymphoid cells (Grosschedl et al., Cell, 38:647, 1984; Adames et al., Nature, 318:533, 1985; Alexander et al., Mol. Cell Biol., 7:1436, 1987); beta-globin gene control region which is active in myeloid cells (Mogram, et al., Nature 315:338-340, 1985; Kollias, et al., Cell 46:89-94, 1986), hematopoietic stem cell differentiation factor promoters; erythropoietin receptor promoter (Maouche, et al., Blood, 15:2557, 1991), etc.; and control regions that exhibit mucosal epithelial cell specificity.

Preferred vectors, particularly for cellular assays in vitro and vaccination in vivo or ex vivo, are viral vectors, such as lentiviruses, retroviruses, herpes viruses, adenoviruses, adeno-associated viruses, vaccinia viruses, baculoviruses, Fowl pox, AV-pox, modified vaccinia Ankara (MVA) and other recombinant viruses with desirable cellular tropism. In a specific embodiment, a vaccinia virus vector is used to infect dendritic cells. In another specific embodiment, a baculovirus vector that expresses EBNA-1 is prepared. Thus, a vector encoding an immunogenic polypeptide can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and vaccination procedures are DNA-based vectors and retroviral vectors. Methods for constructing and using viral vectors are known in the art (see, e.g., Miller and Rosman, BioTechniques, 7:980-990, 1992). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Examples of particular vectors include, but are not limited to, a defective herpes virus 1 (HSV1) vector (Kaplitt, et al., Molec. Cell. Neurosci. 2:320-330, 1991; International Patent Publication No. WO 94/21807, published Sep. 29, 1994; International Patent Publication No. WO 92/05263, published Apr. 2, 1994); an attenuated adenovirus vector, such as the vector described by Stratford-Perricaudet, et al. (J. Clin. Invest. 90:626-630, 1992; see also La Salle, et al., Science 259:988-990, 1993); and a defective adeno-associated virus vector (Samulski, et al., J. Virol. 61:3096-3101, 1987; Samulski, et al., J. Virol. 63:3822-3828, 1989; Lebkowski, et al., Mol. Cell. Biol. 8:3988-3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Adenovirus Vectors.

Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard, et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example). Various replication defective adenovirus and minimum adenovirus vectors have been described (WO94/26914, WO95/02697, WO94/28938, WO94/28152, WO94/12649, WO95/02697 WO96/22378). The replication defective recombinant adenoviruses according to the invention can be prepared by any technique known to the person skilled in the art (Levrero, et al., Gene 101:195 1991; EP 185 573; Graham, EMBO J. 3:2917, 1984; Graham, et al., J. Gen. Virol. 36:59 1977). Recombinant adenovirus is an efficient and non-perturbing vector for human dendritic cells (Zhong et al., Eur. J. Immunol., 29:964, 1999; DiNicola et al., Cancer Gene Ther., 5:350-6, 1998). Recombinant adenoviruses are recovered and purified using standard molecular biological techniques, which are well known to one of ordinary skill in the art.

Adeno-Associated Viruses.

The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques. These viral vectors are also effective for gene transfer into human dendritic cells (DiNicola et al., supra).

Retrovirus Vectors.

In another embodiment the gene can be introduced in a retroviral vector, e.g., as described in Anderson, et al., U.S. Pat. No. 5,399,346; Mann, et al., 1983, Cell 33:153; Temin, et al., U.S. Pat. No. 4,650,764; Temin, et al., U.S. Pat. No. 4,980,289; Markowitz, et al., 1988, J. Virol. 62:1120; Temin, et al., U.S. Pat. No. 5,124,263; EP 453242, EP178220; Bernstein, et al. Genet. Eng. 7 (1985) 235; McCormick, BioTechnology 3 (1985) 689; International Patent Publication No. WO 95/07358, published Mar. 16, 1995, by Dougherty, et al.; and Kuo, et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (WO 90/02806) and the GP+envAm-12 cell line (WO 89/07150). In addition, the recombinant retroviral vectors can contain modifications within the LTRs for suppressing transcriptional activity as well as extensive encapsidation sequences which may include a part of the gag gene (Bender, et al., J. Virol. 61:1639, 1987). Recombinant retroviral vectors are purified by standard techniques known to those having ordinary skill in the art.

Retrovirus vectors can also be introduced by DNA viruses, which permits one cycle of retroviral replication and amplifies tranfection efficiency (see WO 95/22617, WO 95/26411, WO 96/39036, WO 97/19182).

Lentivirus Vectors.

In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest. For a review, see, Naldini, Curr. Opin. Biotechnol., 9:457-63, 1998; see also Zufferey, et al., J. Virol., 72:9873-80, 1998). Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 106 IU/ml for at least 3 to 4 days (Kafri, et al., J. Virol., 73: 576-584, 1999). The vector produced by the inducible cell line can be concentrated as needed for efficiently transducing nondividing cells in vitro and in vivo.

Vaccinia Virus Vectors.

Vaccinia virus is a member of the pox virus family and is characterized by its large size and complexity. Vaccinia virus DNA is double-stranded and terminally crosslinked so that a single stranded circle is formed upon denaturation of the DNA. The virus has been used for approximately 200 years in a vaccine against smallpox and the properties of the virus when used in a vaccine are known (Paoletti, Proc. Natl. Acad. Sci. U.S.A., 93:11349-53, 1996; and Ellner, Infection, 26:263-9,1998). The risks of vaccination with vaccinia virus are well known and well defined and the virus is considered relatively benign. Vaccinia virus vectors can be used for the insertion and expression of foreign genes. The basic technique of inserting foreign genes into the vaccinia vector and creating synthetic recombinants of the vaccinia virus has been described (see U.S. Pat. No. 4,603,112, U.S. Pat. No. 4,722, 848, U.S. Pat. No. 4,769,330 and U.S. Pat. No. 5,364,773). A large number of foreign (i.e. non-vaccinia) genes have been expressed in vaccinia, often resulting in protective immunity (reviewed by Yamanouchi, Barrett, and Kai, Rev. Sci. Tech., 17:641-53, 1998; Yokoyama, et al., J. Vet. Med. Sci., 59:311-22, 1997; and see Osterhaus, et al., Vaccine, 16:1479-81 1998: and Gherardi et al., J. Immunol., 162:6724-33, 1999). Vaccinia virus may be inappropriate for administration to immunocompromised or immunosuppressed individuals. Alternative pox viruses which may be used in the invention include Fowl pox, AV-pox, and modified vaccinia Ankara (MVA) virus. The preferred embodiment to improve the immunogenic potential of these alternative viruses is to deliver the viruses containing EBNA-1 directly to dendritic cells, and then induce the dendritic cells to mature.

Nonviral Vectors.

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et al., Proc. Natl. Acad. Sci. U.S.A. 84:7413-7417, 1987; Felgner and Ringold, Science 337:387-388, 1989; see Mackey, et al., Proc. Natl. Acad. Sci. U.S.A. 85:8027-8031, 1988; Ulmer, et al., Science 259:1745-1748, 1993). Useful lipid compounds and compositions for transfer of nucleic acids are described in International Patent Publications WO95/18863 and WO96/17823, and in U.S. Pat. No. 5,459,127. Lipids may be chemically coupled to other molecules for the purpose of targeting (see Mackey, et al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

Alternatively, non-viral DNA vectors for gene therapy can be introduced into the desired host cells by methods known in the art, e.g., electroporation, microinjection, cell fusion, DEAE dextran, calcium phosphate precipitation, use of a gene gun (ballistic transfection; see, e.g., U.S. Pat. No. 5,204, 253, U.S. Pat. No. 5,853,663, U.S. Pat. No. 5,885,795, and U.S. Pat. No. 5,702,384 and see Sanford, TIB-TECH, 6:299-302, 1988; Fynan et al., Proc. Natl. Acad. Sci. U.S.A., 90:11478-11482, 1993; and Yang et al., Proc. Natl. Acad. Sci. U.S.A., 87:1568-9572, 1990), or use of a DNA vector transporter (see, e.g., Wu, et al., J. Biol. Chem. 267:963-967, 1992; Wu and Wu, J. Biol. Chem. 263:14621-14624, 1988; Hartmut, et al., Canadian Patent Application No. 2,012,311, filed Mar. 15, 1990; Williams, et al., Proc. Natl. Acad. Sci. USA 88:2726-2730, 1991). Receptor-mediated DNA delivery approaches can also be used (Curiel, et al., Hum. Gene Ther. 3:147-154, 1992; Wu and Wu, J. Biol. Chem. 262:4429-4432, 1987). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir, et al., C. P. Acad. Sci., 321:893, 1998; WO 99/01157; WO 99/01158; WO 99/01175).

Vaccine Technology and Immunotherapy

As noted above, the present invention contemplates polypeptide vaccines, and DNA vaccines to deliver an immunogenic EBNA-1 polypeptide to prevent or treat an Epstein Barr Virus infection, or an associated disease (e.g., infectious mononucleosis, endemic Burkitt's lymphoma, Hodgkin's lymphoma, nasopharyngeal carcinoma, T cell lymphoma, gastric carcinoma, and uterine leiomyosarcoma, and possibly chronic diseases such as chronic fatigue syndrome).

The vaccines of the invention are broadly applicable to protect an animal from infection by Epstein Barr Virus. The term "protect" is used herein to mean for the treatment or prevention of Epstein Barr Virus infection. Thus, any animal susceptible to this type of infection can be vaccinated. EBV shows a greater similarity phylogenetically to gammaherpesviruses, herpesvirus saimiri, and bovine herpesvirus 4 than to other classes of herpesvirus (Karlin, et al., J. Virol., 68:1886; 902, 1994; and Bublot, et al., Virology, 190:654-65, 1992). Animal models for EBV occur in some species of New World monkeys (Franken, et al., J. Virol., 69:8011-9, 1995) as well as in mice (Mistrikova and Mrmusova, Acta. Virol., 42:79-82, 1998, Weck, et al., J. Virol., 73:4651-61, 1999; and Simas and Efstathiou, Trends Microbiol., 6:276-82, 1998) and rabbits (Wutzler, et al., Arch. Virol., 140:1979-95, 1995; and Handley, et al., Vet. Microbiol., 47:167-81, 1995). At least one EBV-like herpesvirus that infects monkeys contains a gene with homology to EBNA-1 (Li, et al., Int. J. Cancer, 59:287-95, 1994). Animals infected with EBV-like viruses could be treated with a vaccine of the invention to prevent or treat disease.

Polypeptide Vaccines

As used herein, the term "polypeptide vaccine" refers to a vaccine comprising an immunogenic polypeptide and, generally, an adjuvant. The term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful human adjuvants such as BCG (bacille Calmette-Guerin) and *Corynebacterium parvum*. An example of a preferred synthetic adjuvant is QS-21. Alternatively, or in addition, immunostimulatory proteins, as described below, can be provided as an adjuvant or to increase the immune response to a vaccine. Preferably, the adjuvant is pharmaceutically acceptable.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Sterile water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Certain adjuvants mentioned above, particularly mineral oils and adjuvants containing mineral oils (e.g., Freund's adjuvant) are not acceptable for use in humans.

"DNA" Vaccines

The term "DNA vaccines" is an informal term of art, and is used herein to refer to vaccines delivered by means of a recombinant vector. An alternative, and more descriptive term used herein is "vector vaccine" (since some potential vectors, such as retroviruses and lentiviruses are RNA viruses, and since in some instances non-viral RNA instead of DNA can be delivered to cells). Generally, the vector is administered in vivo, but ex vivo transduction of appropriate antigen presenting cells, such as dendritic cells, with administration of the transduced cells in vivo, is also contemplated. The vector systems described above are ideal for delivery of a vector for expression of an immunogenic polypeptide of the invention.

Vaccination and Immunotherapy Strategies

Various strategies can be employed to vaccinate subjects against Epstein Barr Virus infection. The polypeptide vaccine formulations can be delivered by subcutaneous (s.c.), intraperitoneal (i.p.), intramuscular (i.m.), subdermal (s.d.), intradermal (i.d.), or by administration to antigen presenting cells ex vivo followed by administration of the cells to the subject. Prior to administration to the subject, the antigen presenting cells may be induced to mature.

Similarly, any of the gene delivery methods described above can be used to administer a vector vaccine to a subject, such as naked DNA and RNA delivery, e.g., by gene gun or direct injection.

Vaccination effectiveness may be enhanced by co-administration of an immunostimulatory molecule (Salgaller and Lodge, J. Surg. Oncol., 68:122, 1998), such as an immunostimulatory, immunopotentiating, or pro-inflammatory cytokine, lymphokine, or chemokine with the vaccine, particularly with a vector vaccine. For example, cytokines or cytokine genes such as interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand (Lyman, Curr. Opin. Hematol., 5:192, 1998), as well as some key costimulatory molecules or their genes (e.g., B7.1, B7.2) can be used. These immunostimulatory molecules can be delivered systemically or locally as proteins or by expression of a vector that codes for expression of the molecule. The techniques described above for delivery of the immunogenic polypeptide can also be employed for the immunostimulatory molecules.

Dendritic Cell Targeting.

Vaccination and particularly immunotherapy may be accomplished through the targeting of dendritic cells (Steinman, J. Lab. Clin. Med., 128:531, 1996; Steinman, Exp. Hematol., 24:859, 1996; Taite et al., Leukemia, 13:653, 1999; Avigan, Blood Rev., 13:51, 1999; DiNicola et al., Cytokines Cell. Mol. Ther., 4:265, 1998). Dendritic cells play a crucial role in the activation of T-cell dependent immunity. Proliferating dendritic cells can be used to capture protein antigens in an immunogenic form in situ and then present these antigens in a form that can be recognized by and stimulates T cells (see, e.g., Steinman, Exper. Hematol. 24:859-862, 1996; Inaba, et al., J. Exp. Med., 188:2163-73, 1998 and U.S. Pat. No. 5,851,756). For ex vivo stimulation, dendritic cells are plated in culture dishes and exposed to (pulsed with) antigen in a sufficient amount and for a sufficient period of time to allow the antigen to bind to the dendritic cells. Additionally, dendritic cells may be transfected with DNA using a variety of physical or chemical as described by Zhong et al., Eur. J. Immunol., 29:964-72, 1999; Van Tendeloo, et al., Gene Ther., 5:700-7, 1998; Diebold et al., Hum. Gene Ther., 10:775-86, 1999; Francotte and Urbain, Proc. Natl. Acad. Sci. USA, 82:8149, 1985 and U.S. Pat. No. 5,891,432 (Casares et al., J. Exp. Med., 186:1481-6, 1997). The pulsed cells can then be transplanted back to the subject undergoing treatment, e.g., by intravenous injection. Preferably autologous dendritic cells, i.e., dendritic cells obtained from the subject undergoing treatment, are used, although it may be possible to use MHC-Class II-matched dendritic cells, which may be obtained from a type-matched donor or by genetic engineering of dendritic cells to express the desired MHC molecules (and preferably suppress expression of undesirable MHC molecules.)

Preferably, the dendritic cells are specifically targeted in vivo for expression of EBNA-1. Various strategies are available for targeting dendritic cells in vivo by taking advantage of receptors that mediate antigen presentation, such as DEC-205 (Swiggard et al., Cell. Immunol., 165:302-11, 1995; Steinman, Exp. Hematol., 24:859, 1996) and Fc receptors. Targeted viral vectors, discussed above, can also be used. Additionally, dendritic cells may be induced to mature in vitro after infection by the viral vector, prior to transplantation in vivo.

Mucosal Vaccination.

Mucosal vaccine strategies are particularly effective for many pathogenic viruses, since infection often occurs via the mucosa. Additionally, mucosal delivery of recombinant vaccinia virus vaccines may be able to overcome a pre-existing immunity to poxviruses due to previous smallpox vaccination (Belyakov, et al., Proc. Natl. Acad. Sci. U.S.A., 96:4512-7, 1999). The mucosa harbors dendritic cells, which are important targets for EBNA-1 vaccines and immunotherapy. Thus, mucosal vaccination strategies for both polypeptide and DNA vaccines are contemplated. While the mucosa can be targeted by local delivery of a vaccine, various strategies have been employed to deliver immunogenic proteins to the mucosa (these strategies include delivery of DNA vaccines as well, e.g., by using the specific mucosal targeting proteins as vector targeting proteins, or by delivering the vaccine vector in an admixture with the mucosal targeting protein).

For example, in a specific embodiment, the immunogenic polypeptide or vector vaccine can be administered in an admixture with, or as a conjugate or chimeric fusion protein with, cholera toxin, such as cholera toxin B or a cholera toxin A/B chimera (Hajishengallis, J Immunol., 154:4322-32, 1995; Jobling and Holmes, Infect Immun., 60:4915-24, 1992). Mucosal vaccines based on use of the cholera toxin B subunit have been described (Lebens and Holmgren, Dev Biol Stand 82:215-27, 1994). In another embodiment, an admixture with heat labile enterotoxin (LT) can be prepared for mucosal vaccination.

Other mucosal immunization strategies include encapsulating the immunogen in microcapsules (U.S. Pat. No. 5,075,109, No. 5,820,883, and No. 5,853,763) and using an immunopotentiating membranous carrier (WO 98/0558). Immunogenicity of orally administered immunogens can be enhanced by using red blood cells (rbc) or rbc ghosts (U.S. Pat. No. 5,643,577), or by using blue tongue antigen (U.S. Pat. No. 5,690,938). Systemic administration of a targeted immunogen can also produce mucosal immunization (see, U.S. Pat. No. 5,518,725).

Various strategies can be used to deliver genes for expression in mucosal tissues, such as using chimeric rhinoviruses (U.S. Pat. No. 5,714,374), adenoviruses, vaccinia viruses, or specific targeting of a nucleic acid (WO 97/05267).

EXAMPLES

The present invention will be better understood by reference to the following examples, which are provided by way of exemplification and are not intended to limit the invention.

Example 1

Identification of Positive $CD4^+$ Response to Individual Latent EBV Products

For EBNA-1, we delivered the antigen either exogenously as recombinant protein (Zhang, et al., Nucleic Acids Res., 26:631-7, 1998; Frappier and O'Donnell, J. Biol. Chem., 266:7819-26, 1991), or endogenously via recombinant vaccinia virus constructs. We have uncovered a strong $CD4^+$ T cell response to EBNA-1 presented by either pathway, as monitored by T cell activation and proliferation, IFNγ secretion, and CTL activity. This immune response may be harnessed to resist EBV infection and EBV-associated malignancy.

Material and Methods

Cell Lines.

The EBV transformed B cell lines LRM (HLA-A2, -B44, -DRB1*0401, -DQA1*03, -DQB1*0301, -DP4) (Friede, et al., Biochim. Biophys. Acta., 1316:85-101, 1996) and LG2 (HLA-DRB1*0101, -DQA*0101, -DQB1*0501, -DPA1*0101, -DPB1*0201) (Gorga, et al., J. Biol. Chem., 26:16087-94, 1987) were used. B-LCL were cultured in RPMI-1640+10% FCS+5 mM glutamine+20 μg/ml gentamicin. LCL-BM (HLA-A1, -A3, -B7, -B8, -Cw6, -Cw7, -DR4, -DRw14, -DRw52, -DRw53, -DQw3) and LCL-DC (HLA-A2, -A24, -B38, -B46, -Cw1, -Cw7, -DRB1*1502, -DRB1*0901, -DRB4*01, -DRB5*0101, -DQB1*0502, -DQB1*0303) were generated by culturing PBMC of typed healthy donors with supernatant of the marmoset cell line B95.8 in RPMI-1640+20% FCS+5 mM glutamine+20 μg/ml gentamicin+1 μg/ml cyclosporin A. The BSC40 monkey kidney cell line was grown in DMEM+5% FCS+5 mM glutamine+20 μg/ml gentamicin and used in plaque assays to titer recombinant VV stocks.

Dendritic Cell (DC) and PBMC Preparations.

Leucocyte concentrates (buffy coats) from the New York Blood Center, as well as whole blood from lab donors served as sources of PBMC, isolated by density gradient centrifugation on Ficoll-Paque (Pharmacia). $CD2^+$ PBMC were separated by rosetting with neuraminidase (Calbiochem) treated sheep red blood cells (Colorado Serum Company) followed by red cell lysis with 1.66% ammonium chloride. Where indicated, $CD8^+$ or $CD4^+$ T cells were depleted with Leu2a or OKT8 (for CD8) or HP2/6 (for CD4) antibodies, followed by incubation with sheep-α-mouse-IgG Dynabeads and a magnetic particle concentrator MCP-1 (Dynal, Norway). DCs were generated from $CD2^-$ PBMC as described (Bender, et al., J. Immunol. Methods, 196:121-35, 1996; Romani, et al., J. Immunol Methods, 196:137-51, 1996). $10^6$ CD2$^+$ PBMC/ml were plated in 6-well plates with RPMI-1640+1% single donor plasma+1000 U/ml rhIL-4+1000 U/ml rhGM-CSF+5 mM glutamine+20 μg/ml gentamicin. 100 μl were replaced with 200 μl/ml RPMI-1640+1% single donor plasma+5 mM glutamine+20 μg/ml gentamicin and 1000 U/ml rhIL-4 as well as 1000 U/ml rhGM-CSF were added at day 2, 4 and 6. On day 7, the floating immature DCs were transferred to new plates at $3 \times 10^5$ cells/ml and half of the medium was replaced by monocyte conditioned medium to mature the DCs for two days.

Vaccinia Virus Stock Generation and Infection of DCs.

Recombinant vaccinia viruses were expanded in rabbit kidney RK13 cells. Mature DCs were infected at a MOI of 2 for 1 hour at 37° C. and washed three times. The efficiency of infection was checked after 6 to 12 hours by FACS as described using intracellular staining of a vaccinia early protein of 29 kD with the VV1-6B6 antibody.

Generation of CD4$^+$ T Cell Lines and Clones.

CD8$^-$CD2$^+$ PBMC were stimulated with mature DCs at a ratio of 30:1 (T:DC). For the CM171198 cell line T cells of the healthy donor CM (HLA-A*0201, -A*6801, -B*4402, -B*0702, -C*0501, -C*0702, -DRB1*1501, -DRB1*0401, -DRB5*01, -DRB4*01, -DQB1*0602, -DQB1*0301) were stimulated for 4 weeks with vvEBNA-1ΔGA infected autologous mature DCs with weekly restimulations including autologous CD2$^+$ PBMC as feeders and then alternating with the EBV transformed HLA-DR matched cell line LRM or vvEBNA-1ΔGA infected DCs. The CM110199 cell line was generated from T cells of the donor CM by using DCs that had been incubated with 10 μM of recombinant EBNA-1 protein, added at day 7 together with the maturation stimulus. Purified rEBNA-1 from *E. coli* and baculovirus/insect cell expression systems were alternatively used (Zhang, et al., supra, 1998; Frappier and O'Donnell, supra). Where indicated, *E. coli* derived DNA-C was used as a control protein (*E. coli* control). After 14 days of stimulation in DMEM+5% HS, 50 U/ml rIL-2 was supplemented. For stimulations with the autologous B-LCL, CD2$^+$ PBMC of the healthy donor JT were stimulated for 14 days with the irradiated autologous LCL-JT at a B cell to T cell ratio of 1:10 in DMEM+5% human serum+10 U/ml IL-2 (Lymphocult, Dreieich, Germany). Where indicated, CD4$^+$ or CD8$^+$ T cells were depleted.

EBNA-1 specific CD4$^+$ CTL were cloned under limiting dilution conditions by stimulating $10^5$ CD8$^-$CD2$^+$PBMC with $10^4$ autologous B-LCL from leukocyte concentrates in 96 well plates for 14 days with one restimulation at day 7. IL-2 was added to the cultures during the restimulation to a final concentration of 10 U/ml (Lymphocult). Microcultures were tested in split well $^{51}$Cr release assays against autologous DCs infected with vvEBNA-1ΔGA or vvTK$^-$, autologous B-LCL or LCL721.221. At this initial T cell number, <30% of the wells developed CTL indicating >90% probability for clonality of the responders (Taswell, et al., J. Exp. Med., 151:1372-85, 1980).

FACS Analysis of Stimulated CD4$^+$ T Cell Populations and PBMC.

Mature DCs were infected with recombinant VV at an MOI of 2, or with influenza virus (PR8, Puerto Rico/8/34, Spafas Inc., Storrs, Conn.) at a MOI of 0.5 for 1 hour at 37° C. in RPMI-1640+5% HS. DCs were washed twice and $3 \times 10^3$ added to $10^5$ CD8$^-$ CD2$^+$ PBMC in 96 well plates for 7 days. At day 7, the cultures were restimulated with $10^5$ PBMC and $3 \times 10^3$ DCs per well and incubated for another 7 days. The cultures were restimulated with $10^5$ irradiated (3000 rad) PBMC and $3 \times 10^3$ DCs per well and incubated for another 7 days. After 14 days, cultures were stained for 30 minutes on ice with 1 μl Simultest CD4-FITC/CD8-PE (Becton Dickinson) in 100 μl PBS+1% FCS+0.005% sodium azide. After 3 washes, cultures were analyzed on a FACScan (Becton Dickinson). CD56 antibody staining (PharMingen) used PE-goat αmouse-IgG antibody (Biosource) as secondary. PBMC were typed for HLA-DR4 using HLA-DR4 antibody (Accurate) as primary and FITC-goat α-mouse IgG antibody (Biosource) as secondary.

ELISPOT Assay for IFNγ Secreting Cells.

MAHA S45 plates (Millipore) were coated with 10 μg/ml αIFNγ antibody 1-DIK (MABTECH) in 50 μl/well 50 mM Na$_2$CO$_3$, pH 9.5, overnight at 4° C. Plates were washed 4 times with PBS and blocked with DMEM+5% HS for 1 hour at 37° C. Afterwards, $10^5$ responder T cells and $3 \times 10^3$-$10^4$ stimulator DCs were added per well and incubated for 1-2 days at 37° C. Then the plates were washed 4 times with PBS+0.05% Tween 20 and incubated for 2 hours at 37° C. with 1 μg/ml biotinylated αIFNγ antibody 7-B6-1 (MABTECH) in 50 μl/well PBS. Afterwards the plates were again washed for 4 times with PBS+0.1% Tween 20 and incubated with 20 minutes at room temperature preassembled avidin-peroxidase-complexes Vectastain ABC kit (Vector laboratories) for 1 hour at room temperature. After another 4 washes with PBS+0.1% Tween 20, 50 μl/well of stable DAB (Research Genetics) was added for 5 minutes at room temperature. Plates were washed 3 times with water and air dried. SFC/$10^5$ cells were counted using a stereomicroscope (mean counts of triplets). Where indicated, αHLA-DR antibody L243 (Lampson, and Levy, J. Immunol., 125:293-9, 1980) or αHLA-A, B, C antibody B-H9 (Biosource) was added to 5 μg/ml.

Proliferation Assays.

Responder T cells ($10^5$) were incubated with $3 \times 10^3$-$10^4$ stimulator DCs for 5 days in DMEM+5% HS. 1 μCi $^3$H-Thymidine was added/well overnight and harvested by an automatic device (Skatron) and counted in a Betaplate 1205 (LKB Wallac). Counts represent mean values of triplicates.

$^{51}$Cr Release Assay.

Targets were labeled with 50 μCi Na$_2$$^{51}$CrO$_4$ for 45 minutes at 37° C. Labeled targets were incubated for 4 hours with CTL in RPMI+10% FCS+2 mM glutamine. The supernatant was harvested using a Skatron harvesting system and radioactivity measured in a γ counter (1470 Wizard, Wallac, Turku, Finland). Percent specific lysis was ([cpm experimental well–cpm spontaneous release]/[cpm maximum release–cpm spontaneous release])×100%. Spontaneous release was determined by incubating the labeled targets with medium, and maximum release by incubating targets in 1% Triton X-100 solution.

Results

Figure 1E:
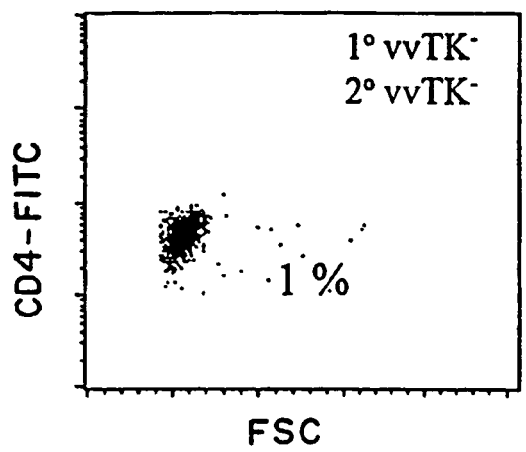
Figure 1F:
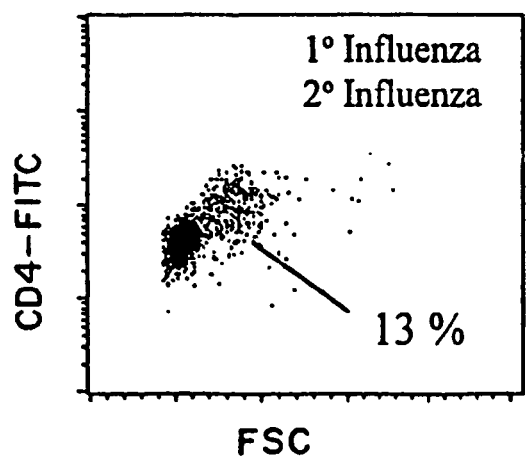
Figure 2A:
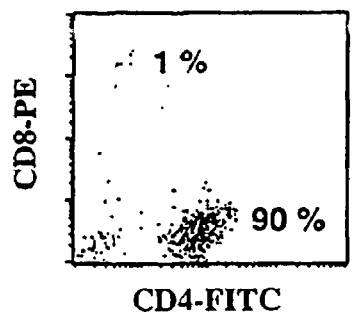
FIGS. 2A, 2B, 2C, and 2D. Recognition of EBNA-1 provided to DCs by endogenous and exogenous pathways. A. CD4+ (CD4-FITC) versus CD8+ (CD8-PE) content. B. CD56+ (CD56-PE) content. C. IFNγ spot forming cells/$10^5$ cells stimulated with recombinant baculovirus expressed EBNA-1 protein loaded DCs (DC+bEBNA-1) and without loading (DC). D. Spot formation of the line upon incubation with vvTK− infected DCs (DC+vvTK−), vvEBNA-1ΔGA infected DCs (DC+vvEBNA-1ΔGA), vvT7 infected DCs (DC+vvT7), vvEBNA-1 infected DCs (DC+vvEBNA-1) and vvEBNA-1/vvT7 double infected DCs (DC+vvEBNA-1+vvT7). In the same figure the MHC restriction is analyzed using the antibodies L243, αHLA-DR, (+L243) and B-H9, αHLA class I, (+B-H9) for blocking. In addition, spot formation upon stimulation with the HLA-DR4+ B-LCL, LRM (LRM), vs. the HLA-DR4− B-LCL, LG2 (LG2), is shown.
Figure 2B:
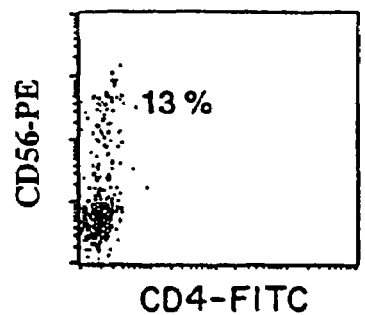

In order to identify latent EBV antigens that are recognized by CD4$^+$ T cells, CD8$^-$CD2$^+$ peripheral blood mononuclear cells (PBMC) were stimulated for 2 weeks with autologous DCs infected with recombinant vaccinia virus constructs expressing the EBV latent antigens EBNA-1, 3A, 3B, 3C and LMP1, 2. Responses were assessed by the presence of enlarged CD4$^+$ T cells ("blasts") upon two stimulations with DCs. Specifically, one of a panel of EBV recombinants was used to stimulate the CD4$^+$ T cells in the first week of culture, and then the cultures were divided in two and restimulated a second week with the original recombinant vaccinia virus or with vvTK$^-$ as control. We looked for specific blastogenesis to the primary EBV recombinant. All 7 donors showed strong responses to vvEBNA-1 (Table 1; FIGS. 1A, B). The response to the negative control (vvTK−) was weak (FIG. 1E) in all but one donor who was excluded from Table 1. All donors responded to influenza infected DCs which were used as a positive control (FIG. 1F). A smaller proportion of the 7 donors responded to other vvEBV constructs, i.e., EBNA3B (4/7), EBNA3A (1/7), and LMP1 (3/7) (Table 1A). To ensure that the recombinant vaccinia viruses infected a comparable proportion of the mature DCs, the intracellular expression of the 29 kD vaccinia early protein was measured by flow cytometry. Reproducibly, 40-60% of DCs were infected with the recombinant vaccinia viruses. The reliability of the CD4+ recognition of EBNA-1 could be confirmed in an ELISPOT assay for IFNγ secretion, where EBNA-1 was the EBV latency gene that was preferentially recognized (Table 1B). We regard these CD4+ T cell responses to EBNA-1 in vitro to reflect initial priming by EBV infection of the blood donors in vivo, since we did not see blastogenesis in two weeks if we stimulated neonatal T cells from blood cord specimens with EBNA-1. We verified that our donors showed HLA class II diversity since only 2 out of 7 expressed HLA-DR4.

Figure 2C:
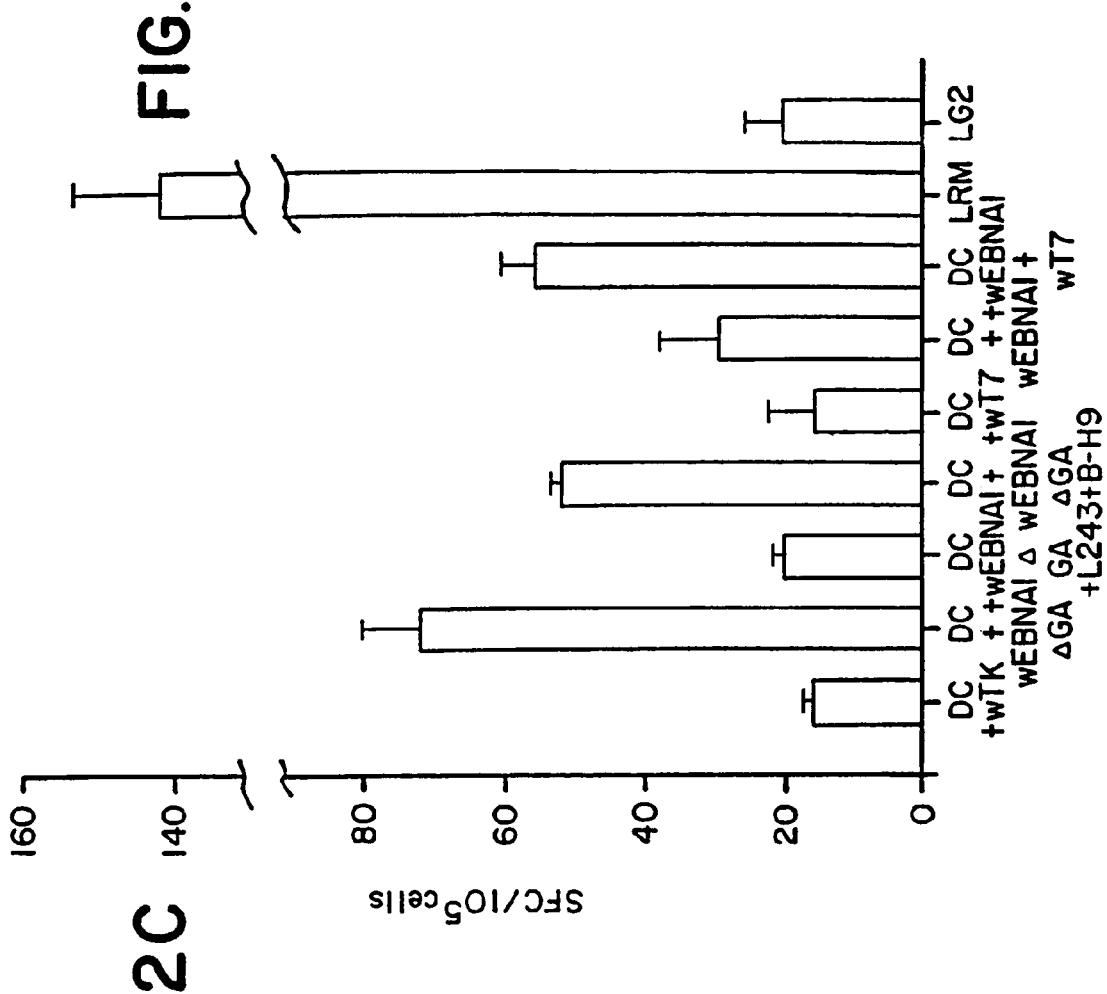
Figure 2D:
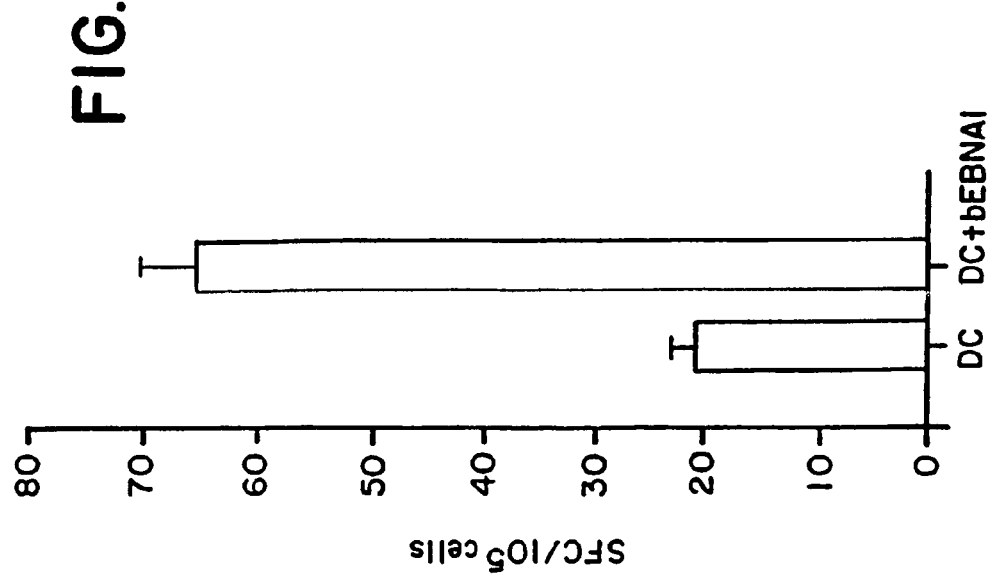

EBNA-1 (FIGS. 2C, 3A). Reactivity could be measured as IFNγ secretion in ELISPOT assays (FIG. 2) or by proliferation assays (FIG. 3). The T cell responses were blocked by addition of an anti-HLA-DR antibody, L243, but not by an anti-HLA class I antibody, B-H9 (FIG. 2D). As expected, the presence of the GA repeat domain had no effect on this HLA-DR restricted presentation, since DCs infected with full length vvEBNA-1 were also recognized by CM171198, as long as EBNA-1 expression was enhanced by coinfection with vvT7 to drive the T7 promotor for EBNA-1 in this construct (FIG. 2D). Although there may be gly/ala minus forms of EBNA-1 in DCs infected with full length EBNA-1 expressing vaccinia viruses, we also observe specific T cell recognition of B-LCL (FIG. 3), in which only full length EBNA-1 is detected (see, Blake et al., Immunity, 1997, 7:791-802). This further suggests that the gly/ala repeat has no influence on MCH class II processing and presentation.

Additionally, the EBV negative Ramos Burkitt lymphoma cell line, stimulated EBNA-1 specific T cells at a level comparable to DCs infected with vaccinia EBNA-1. However, Ramos cells were not capable of capturing EBNA-1 from

TABLE 1

CD4+ T lymphocyte responses to dendritic cells infected with recombinant vaccinia-EBV vectors.

| Donor No. | vvTK− | vvEBNA-1 | vvEBNA3A | vvEBNA3B | vvEBNA3C | vvLMP1 | vvLMP2A | vvBMLF1 | Influenza |
|---|---|---|---|---|---|---|---|---|---|
| A: Percentages of blasting CD4+ T lymphocytes upon restimulation with specific antigen. | | | | | | | | | |
| 1 | 4* | 17 (2#) | 22 (8) | 11 (3) | n.d. | 23 (3) | 8 (4) | 3 (3) | 17 (6) |
| 2 | 2 | 15 (3) | 6 (2) | 17 (8) | 8 (3) | 8 (2) | 3 (2) | 0 (0) | 12 (3) |
| 3 | 0 | 11 (6) | 0 (0) | 19 (8) | 0 (0) | 30 (18) | 0 (0) | 0 (0) | 28 (10) |
| 4 | 1 | 11 (6) | 1 (1) | 12 (7) | 2 (1) | 14 (10) | 1 (0) | 1 (0) | 35 (6) |
| 5 | 1 | 15 (4) | 1 (1) | 4 (2) | 3 (1) | 6 (1) | 1 (1) | 0 (1) | 13 (10) |
| 6 | 2 | 8 (3) | n.d. | 2 (2) | 1 (2) | 5 (1) | 3 (3) | n.d. | 15 (7) |
| 7 | 3 | 11 (6) | 2 (2) | 2 (2) | 1 (1) | 3 (2) | 3 (1) | 3 (3) | 34 (11) |
| B. IFNγ producing CD4+ lymphocytes upon restimulation with specific antigen. | | | | | | | | | |
| 5 | 7 ± 1$ | 23 ± 1 (7 ± 4&) | 5 ± 4 (7 ± 4) | 2 ± 1 (5 ± 1) | 6 ± 2 (5 ± 1) | 4 ± 1 (2 ± 1) | 10 ± 4 (6 ± 1) | 1 ± 1 (2 ± 1) | 79 ± 3 (9 ± 1) |
| 6 | 3 ± 1 | 88 ± 8 (37 ± 1) | n.d. | 5 ± 1 (4 ± 2) | 3 ± 1 (2 ± 2) | 4 ± 2 (3 ± 1) | 6 ± 3 (2 ± 2) | n.d. | 88 ± 3 (27 ± 6) |
| 7 | 1 ± 1 | 16 ± 1 (4 ± 1) | 4 ± 2 (2 ± 2) | 2 ± 1 (3 ± 0) | 2 ± 0 (3 ± 0) | 2 ± 2 (2 ± 1) | 6 ± 4 (1 ± 0) | 4 ± 2 (5 ± 1) | 77 ± 2 (5 ± 1) |

*Incubations were performed with vaccinia virus infected autologous mature DCs and monitored by flow cytometry after two stimulations.
Values in brackets reflect blasted subpopulations that were restimulated with vvTK− infected DCs as control.
$Spot forming cells per $10^5$ cells after overnight incubation with Vaccinia virus infected autologous mature DCs (mean values of triplicates are shown).
&Values in brackets reflect reactivity against vvTK− infected DCs as control.

We then pursued the requisite MHC restriction elements and processing pathways by generating cell lines, initially from an HLA-DR4+ donor, CM. We could then test the reactivity of the T cell lines with DCs that had been infected with recombinant vaccinia viruses expressing EBNA-1 or pulsed with soluble EBNA-1 protein. One line, CM171198, was established by stimulating CD8−CD2+ PBMCs with EBNA-1 processed endogenously. Therefore, the APCs were either the DR4-matched B-LCL LRM or autologous DCs infected with vvEBNA-1ΔGA. The latter construct was deleted of the GA repeat which blocks MHC I presentation and also reduces expression of EBNA-1. The other line, CM110199, was stimulated with exogenously supplied EBNA-1. Therefore, during their final maturation, the DCs were exposed to recombinant EBNA-1 protein expressed either in E. coli or in a baculovirus-insect cell-system. After one month of culture, both lines contained predominantly CD4+ T cells, 90% in CM171198 (FIG. 2A) and 76% in CM110199. Both lines performed similarly in the assays that follow, and therefore, only the data from CM171198 are shown.

The CD4+ T cell lines recognized DCs that were infected with vvEBNA-1ΔGA or exogenously supplied recombinant allogenic LCL or from high doses of EBNA-1 protein. This data further supports the finding that EBNA-1 is processed endogenously in B cell lines.

In addition to DCs charged with EBNA-1, the CM171198 cell line recognized EBV transformed B-LCL without further addition of antigen. However, the LCL targets had to be matched at the DR4 allele. Thus, the DR4+ LCL (LRM and LCL-BM) induced proliferation, but the DR4− cells (LG2 and LCL-DC) did not (FIG. 3B). Therefore, EBNA-1 specific CD4+ T cells seem to recognize EBV-transformed B cells.

Figure 4A:
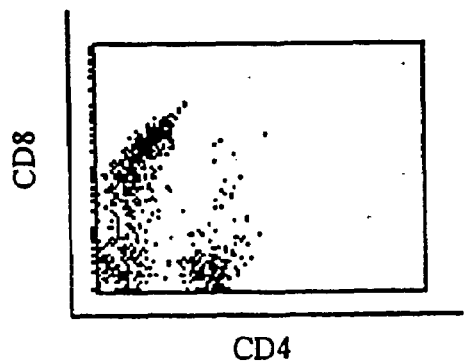
FIGS. 4A, 4B, 4C, 4D, 4E, 4F, 4G, and 4I. Cytotoxic activity and EBV latent antigen specificity of T cell subsets. The left column (A-C) shows the CD8 vs. CD4 FACS stainings of three PBMC responder populations: (A) CD2+PBMC, (B) CD8−CD2+PBMC and (C) CD4−CD2+PBMC. The middle column (D-F) displays the observed lysis of autologous LCL (LCL-JT; solid circles) and T2 cells (T2; open circles) by these responders. In the right column (G-I) the EBV latent antigen specificity of the three responder populations was investigated in an ELISPOT assay (E1: vvEBNA-1ΔGA, E2: vvEBNA2, E3B: vvEBNA3B, E3C: vvEBNA3C, L1: vvLMP1, L2a: vvLMP2A, B1: vvBMLF1, LCL: LCL-JT).
Figure 4B:
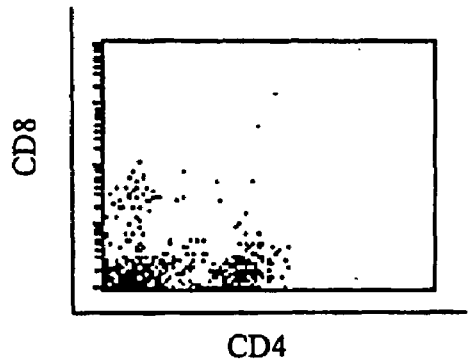
Figure 4C:
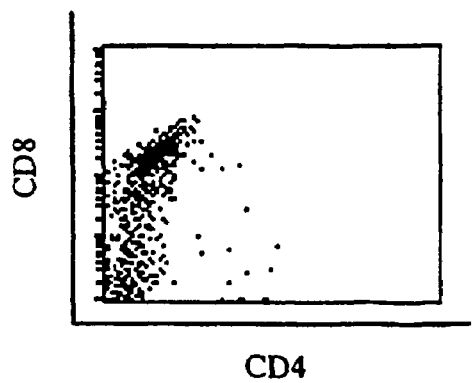
Figure 4G:
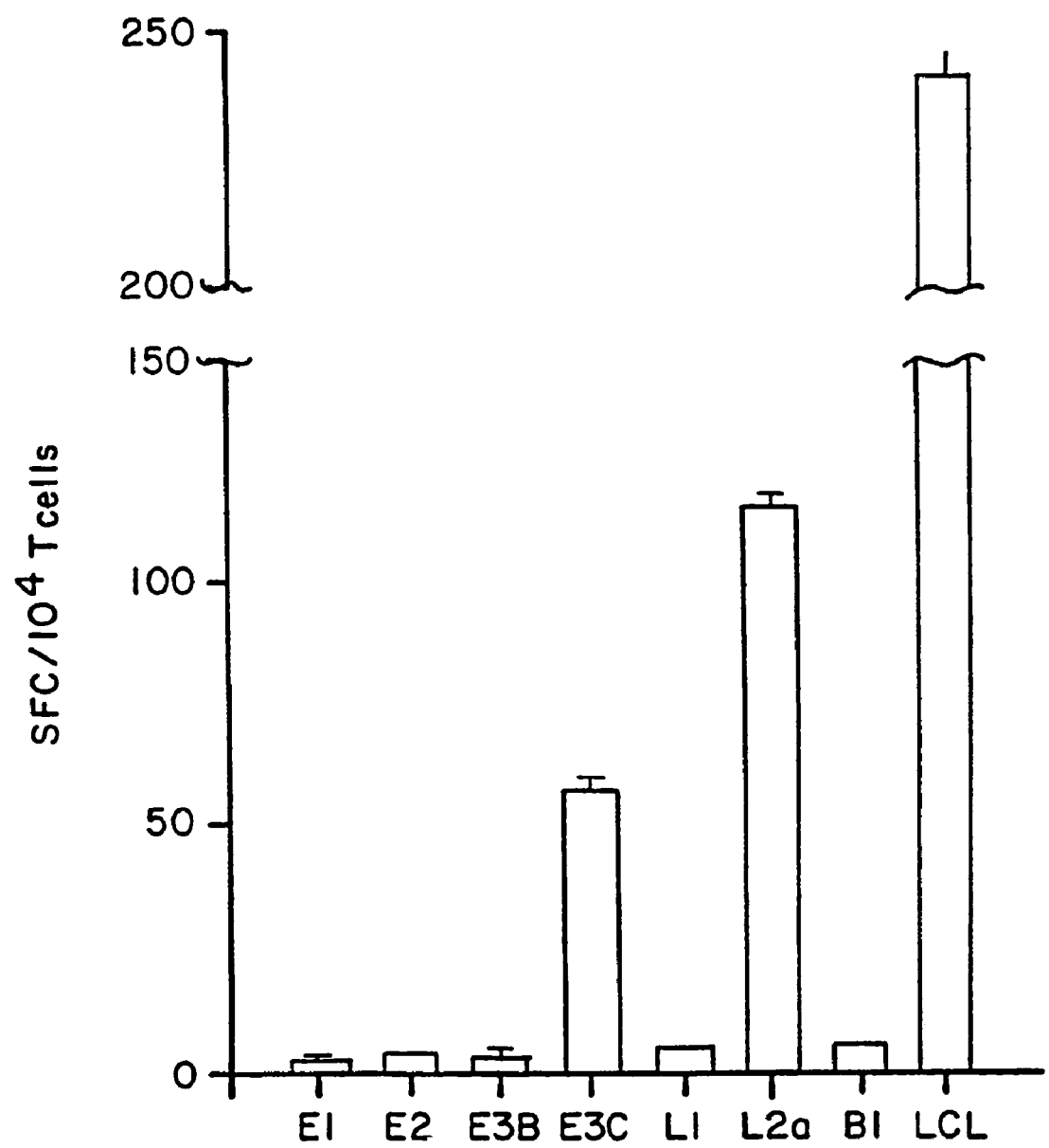
Figure 4H:
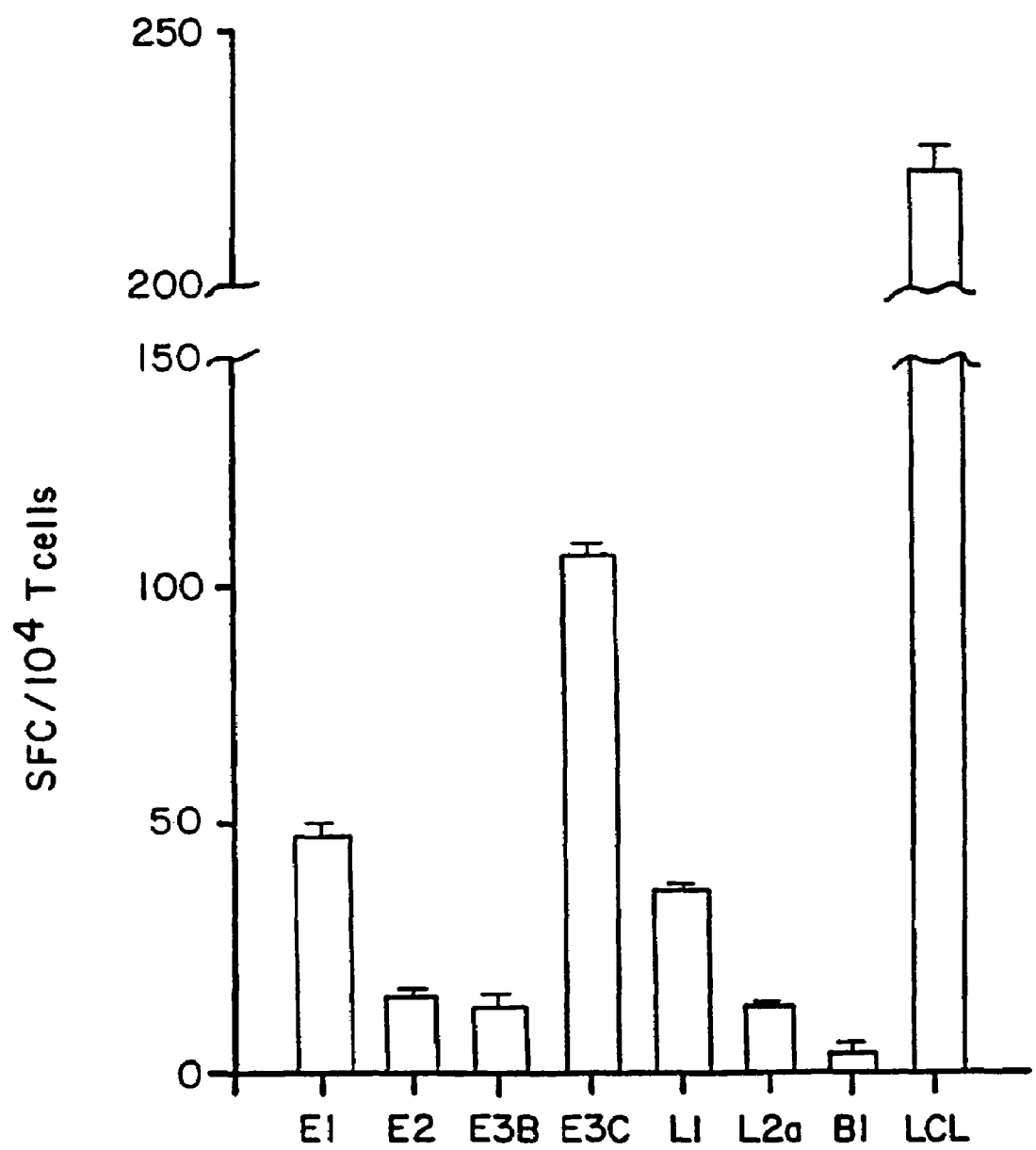
Figure 4I:
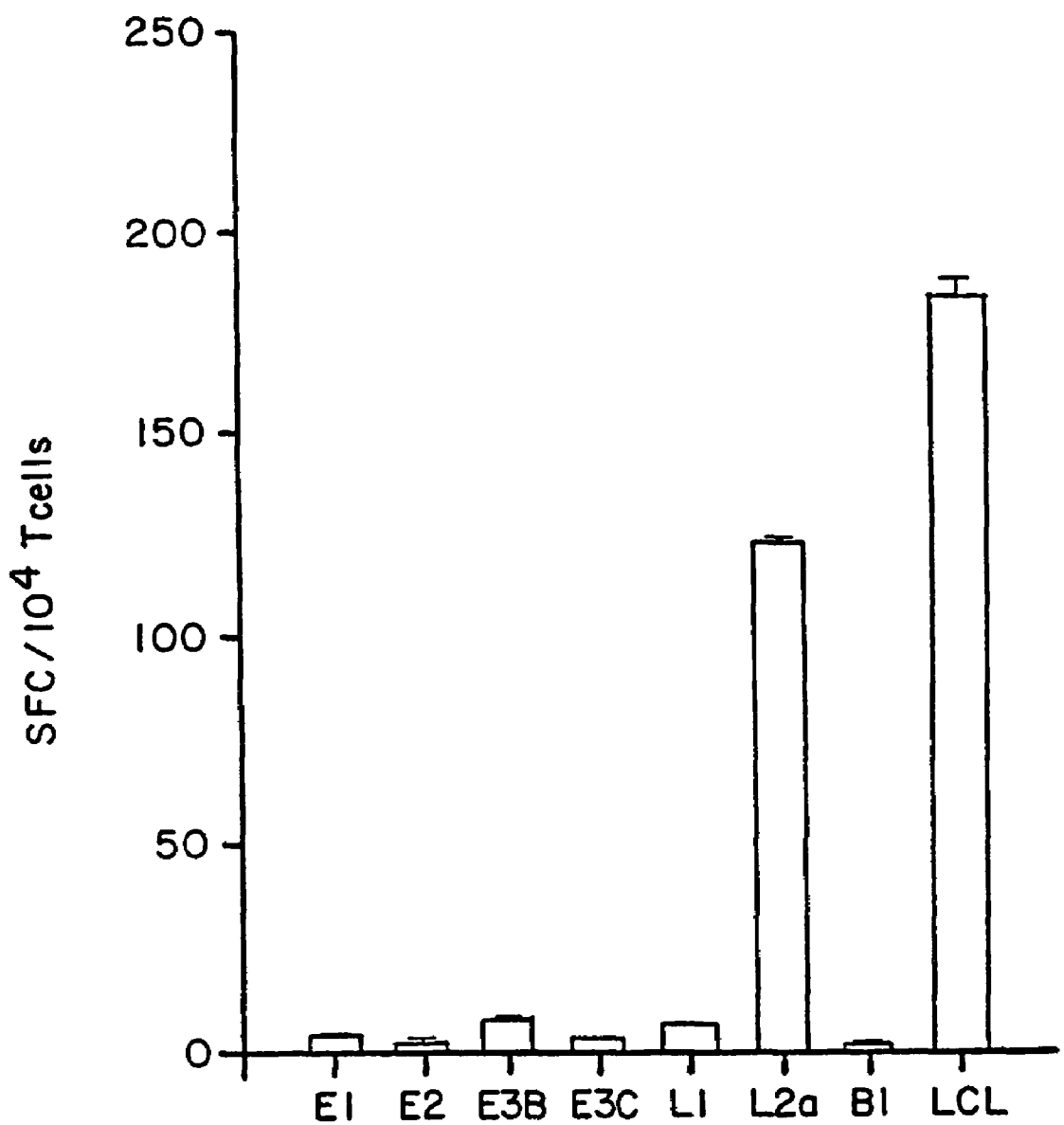

To determine if EBNA-1 also was an antigen for CD4+ CTL responses, we stimulated CD8−CD2+ PBMCs from another (but HLA-DR4−) healthy donor, JT, with irradiated autologous B-LCL (which express all known latent EBV antigens (Kieff and Liebowitz, supra)) for 14 days with one restimulation after 7 days. In parallel to the stimulation of CD8−CD2+ T cells, we followed responses to B-LCL in bulk CD2+ T cells and in CD4−CD2+ T cells. $^{51}$Cr-release assays were first performed to document lytic activity against autologous B-LCL, and then the EBV specificity was assessed using DC targets that had been infected with the different recombinant EBV constructs. The content of the stimulated T cell populations was determined by FACS. CD8-depleted responders were enriched for CD4+ cells (FIG. 4B), CD4-depleted responders were enriched for CD8+ cells (FIG. 4C) and the bulk T cells had a CD4/CD8 ratio of 1:2 (FIG. 4A-C). All contained about 25% CD56+ NK cells. All of the stimulated populations, i.e., bulk T cells (FIG. 4D) and CD4 (FIG. 4E) or CD8 (FIG. 4F) enriched cells, killed autologous B-LCL and showed less recognition of the T2 cell line. The latter can be probably attributed to the contaminating NK cells. Remarkably however, the EBV targets for the different T cell responders were quite different (FIG. 4, G-I). The CD4+ T cells preferentially recognized EBNA-1, EBNA3C and LMP1 (FIG. 4H), while CD8+ T cells recognized LMP2a (FIG. 4I). Bulk T cells recognized EBNA3C, the dominant antigen for CD4+ cells in this donor, and LMP2a, the dominant antigen for CD8+ T cells (FIG. 4G).

Figure 5A:
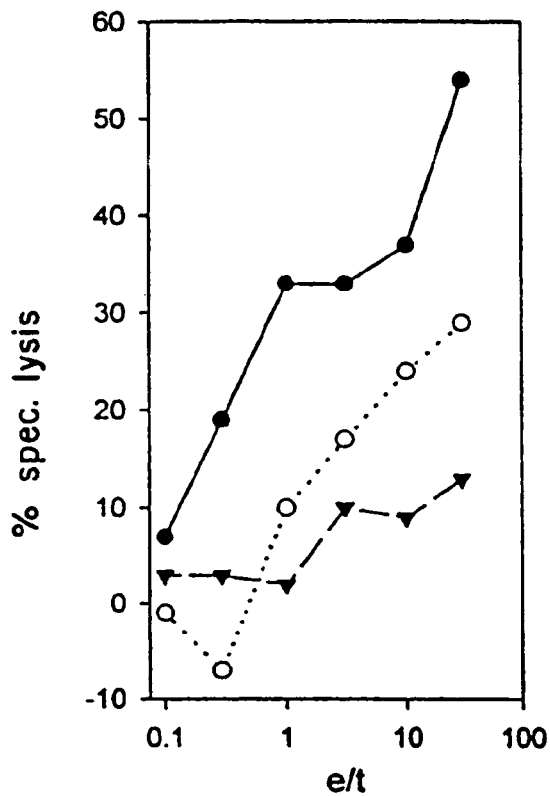
FIGS. 5A, 5B, 5C, 5D, 5E, and 5F. HLA-DR restriction and EBNA-1 recognition by CTL subsets. The effectors, as shown on the top, were either CD2+PBMC (A, D), CD8−CD2+PBMC (B, E) or CD4−CD2+PBMC (C, F). The top row (A-C) shows cytolysis of autologous B-LCL (LCL-JT) in the presence (open circles, dotted line) or absence (solid circles) of 5 μg/ml L243, αHLA-DR antibody (LCL-JT+L243). T2 cells (solid triangles) were used as a control. The bottom row (D-F) shows lytic activity against autologous B-LCL (LCL-JT; open triangles) in comparison to autologous DCs pulsed with E. coli derived control protein (eControl; solid circles), E. coli derived EBNA-1 protein (eEBNA-1; open circles) or baculovirus/insect cell derived EBNA-1 protein (bEBNA-1; solid triangles).
Figure 5B:
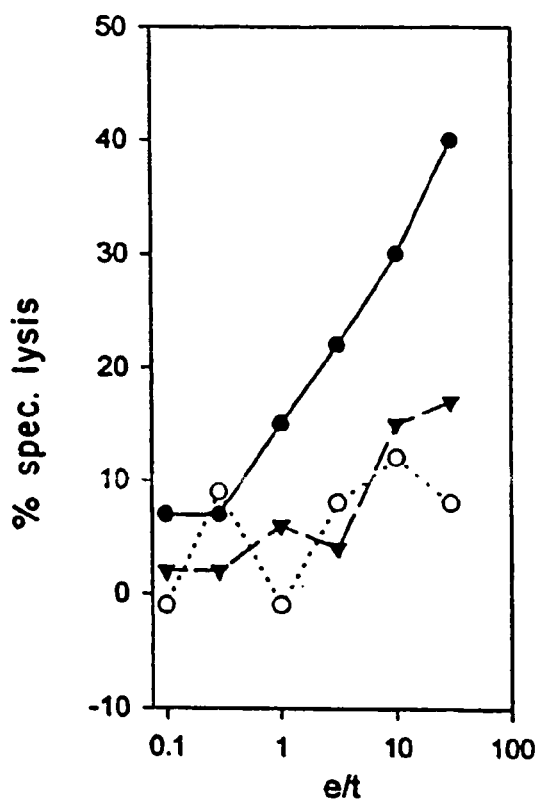
Figure 5C:
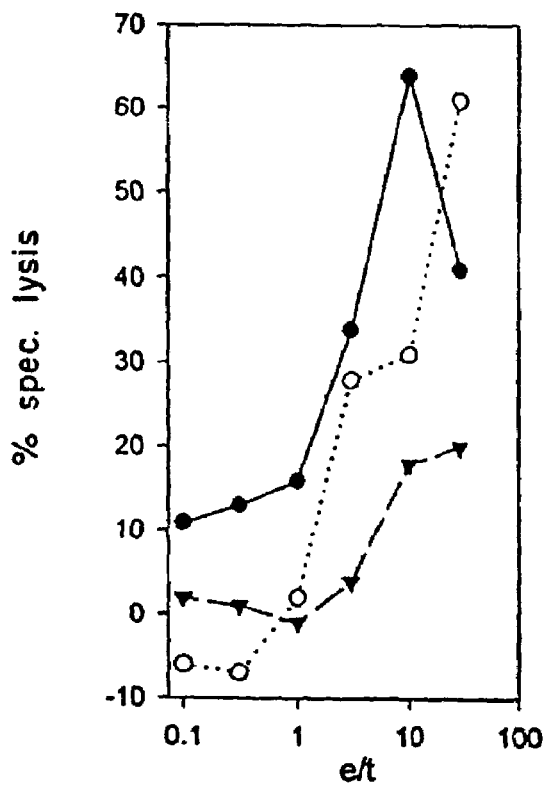
Figure 5D:
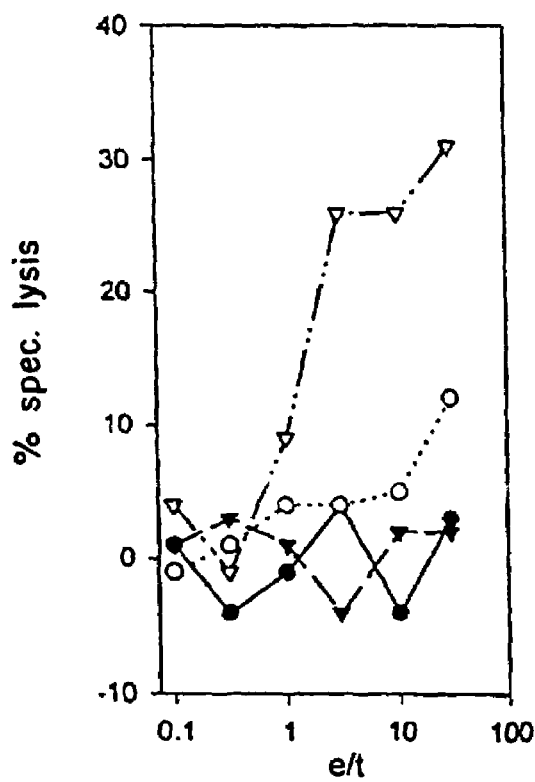
Figure 5E:
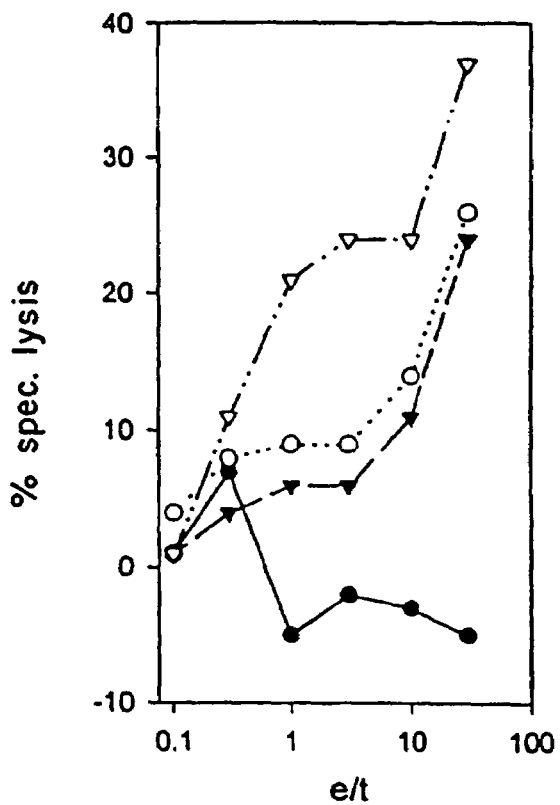
Figure 5F:
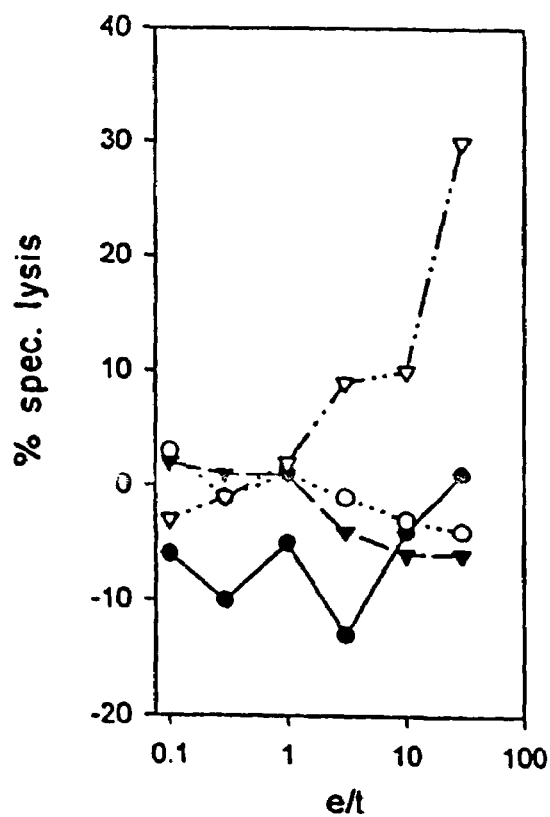

The CTL function of the stimulated cells was further assessed. As expected, the killing of autologous B-LCL was completely blocked by L243 anti-HLA-DR antibody only when CD4-enriched populations were tested (FIG. 5B). LCL-JT killing by CD8-enriched cultures was not blocked by the anti-HLA-DR antibody (FIG. 5C), and killing by the bulk T cells only partially inhibited (FIG. 5A). The CD4-enriched T cells also lysed EBNA-1 pulsed DCs (FIG. 5E), while CD8-enriched cultures did not (FIG. 5F) and bulk T cells only weakly (FIG. 5D). Therefore, CD4 T cells can lyse autologous B-LCL, and one of the EBV encoded targets is the EBNA-1 latency gene.

Figure 6B:
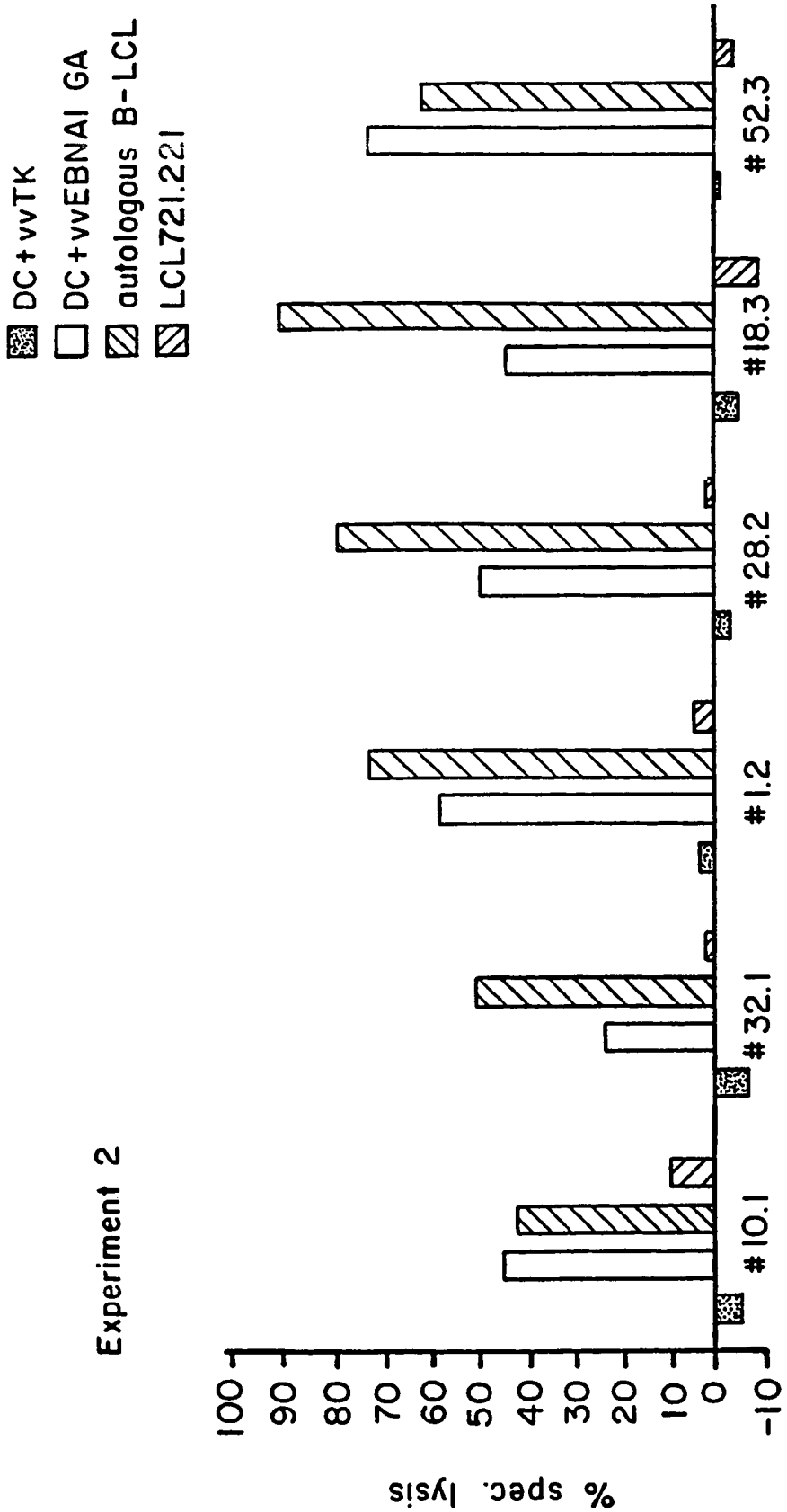

To prove that individual CD4+ T cells lysed DCs charged with EBNA-1 as well as B-LCL expressing EBNA-1 endogenously, we studied CD4+ CTL cloned by limiting dilution from cryopreserved T cells stimulated with autologous B-LCL. The DCs, T cells and autologous B-LCL were derived from leukocyte concentrates. All EBNA-1 specific CD4+ CTL could kill the autologous B-LCL (FIGS. 6A, 6B). Recognition of DCs infected with the vvTK− control vector or LCL721.221, a HLA class I NK target, was poor by these clones (FIGS. 6A, 6B). Therefore, CD4+ T cells can lyse autologous B-LCL, and one target is EBNA-1.

These findings demonstrate CD4+ T cell reactivity to EBV latently infected B cells. The nuclear antigen EBNA-1 is repeatedly recognized by CD4+ T cells from healthy adults. The CD4+ T cells are capable of proliferation, cytokine secretion and cytolytic activity. Other EBV latency antigens that we tested (EBNA3A, 3B, 3C; LMP1, 2; Table 1) can be recognized by CD4+ T cells but less reliably than EBNA-1. A single EBNA-1 specific CD4+ T cell clone has been described previously (Khanna, et al., Int. Immunol., 9:1537-43. 1997). This clone only killed targets with exogenously processed EBNA-1, probably due to low affinity. The CD4+ T cells described here are readily identified in bulk cultures and recognize EBNA-1 processed by exogenous and endogenous routes, even at physiological concentrations as presented on HLA-DR products of transformed B-LCL. However in more general terms, the successful processing of an endogenous nuclear antigen onto MHC class II is not unusual. When peptides have been eluted from the MHC class II molecules of B cells, only ~20% of the identified peptides are of exogenous origin (Rammensee, et al., in MHC ligands and peptide motifs, Springer: Lands Bioscience, Austin, 1997). The endogenously derived peptides also include nuclear antigens like $CBF3_{59-74}$ on $H2-A^d$ (Rudensky, et al., Nature, 353:622-7, 1991), Histone $H3_{110-127}$ on HLA-DRB1*0405 (Friede, et al., supra, 1996), $c-myc_{371-385}$ on HLA-DRB1*0801 (Chicz, et al., J. Exp. Med., 178:27-47, 1993), and Histone $H4_{31-45}$ on HLA-DRB 1*1401 (Harris et al., Blood, 87:5104-12, 1996).

EBNA-1-specific CD4+ T cells could provide direct resistance to EBV transformed cells, e.g. through their lytic function, or by sustaining the CD8+ CTL response to other lymphoma-related EBV products such as LMP-1 and LMP-2. A good deal of circumstantial evidence for CD4+ T cell protection against gamma herpesviruses exists in the literature:

a) The CTL response to EBV in the cotton top tamarin *Sanguinis oedipus* (Cleary et al., Science, 228:72204, 1985) is to a large extent MHC class II restricted (Wilson et al., Clin. Exp. Immunol., 103:199-205, 1996). No MHC class I restricted, EBV-specific CTL have been found to date in this new world monkey, and this species lacks classical MHC class I (although it does express homologues of nonclassical class I genes like HLA-G and HLA-F (Watkins, et al., Nature, 346:60-3, 1990)).

b) γ-herpesvirus infection in mice by MHV-68 can be controlled by IFNγ secreting CD4+ T cells (Christensen, et al., Proc. Natl. Acad. Sci. USA, 96:5135-5140, 1999).

c) Control of the growth of Burkitt's lymphoma cells by CD4+ T cells has been described in culture (Schattner, et al., Blood, 88:1375-82, 1996), and this lymphoma only expresses a single EBV gene, EBNA-1.

d) Early in HIV-1 infection, when CD4+ T cell counts are still high but CD4+ T cell function starts to be compromised, patients can develop Burkitt's lymphomas rather than mononucleosis (Levine, Blood, 80:8-20, 1992).

e) An impairment of the CD4+ response is thought to be responsible for the EBV-induced infectious mononucleosis seen in X-linked lymphoproliferative disease patients who have a mutation or deletion in SAP, an inhibitor of the T cell costimulatory molecule SLAM or CDw150 (Sayos, et al., Nature, 395:462-9, 1998).

f) An antibody response to EBNA-1 is detectable in most donors (Rowe, et al., J. Gen. Virol., 69:1217-28, 1988), consistent with the presence of CD4+ helper cells, and EBNA-1 was the only reliable EBV antigen for CD4+ responses that we observed.

These observations together with the direct evidence for CD4+ T cell responses to EBNA-1, described here, suggest that the latter T cells might provide resistance to Burkitt's, Hodgkin's, and other EBV-associated malignancies in most healthy EBV infected individuals. Our data also suggest that EBNA-1 may be used as an antigen to prevent and treat such malignancies.

For example, immunotherapy of nasopharyngeal carcinoma with EBNA-1 pulsed dendritic cells should result in remission. Immunotherapy appears to be critical for effectively treating nasopharyngeal carcinoma (Tsukuda et al., J. Cancer Res. Clin. Oncol., 120:115, 1993).

The ability to treat nasopharyngeal carcinoma represents a significant step forward in managing this disease. Previous treatments include radiotherapy, surgical resection, and chemotherapy (Sangurineti and Corvo, Oncol. Rep., 6:377, 1999). However, this form of cancer is difficult to treat, and treatment regimens, particularly radiotherapy, cause significant collateral damage to the brain, such as radiation-induced bilateral optic neuropathy (Wijers et al., Stohlenther. Oncol., 175:21, 1999).

Example 2

The EBNA-1-Specific CD4+ T Cells are Primarily $T_H1$ in Function

Example 1 discloses a consistent EBNA-1-specific, CD4+ T cell response in blood cells from healthy donors. To detect these CD4+ T cells, some of which could secrete IFNγ, a 2-week stimulation culture was used in which DCs were the antigen presenting cells and purified CD4+ T cells were the responders. This example establishes that the EBNA-1-specific CD4+ T cells are skewed toward a $T_H1$ phenotype, and that this response can be detected in vivo.

Material and Methods

Dendritic Cell and CD4+ T Cell Preparation.

For the generation of DCs, see Example 1 above. In some experiments, a rEBNA-1 protein or rPCNA control protein was added to the DC cell culture at the indicated concentrations with the maturation stimulus. For use as target in $^{51}Cr$ release assays, DCs were pulsed with either 1 μg/ml of rEBNA-1 protein or of the rPCNA control prior to use as targets. For positive selection of CD4+ T cells, CD 14− cells were treated with a monoclonal anti-human CD4 antibody conjugated to magnetic microbeads (Miltenyi). T cells and DCs were used fresh or after cryopreservation in FCS and 5% DMSO.

DC Infection with Recombinant Vaccinia Viruses.

Viruses were as previously described (Subklewe, et al., Eur. J. Immunol., 1999, 29:3995-4001). Mature DCs were infected with recombinant vaccinia vectors expressing thymidine kinase (vvTK−) as a negative control or vvEBNA-1ΔGA at an MOI of 2 for 1 hour at 37° C., and washed 3 times in medium with 5% human serum. Infection was verified at 6-12 hours by intracellular staining as described previously (Subklewe et al., 1999, supra) using VV1-6B6 antibody to a vaccinia early protein followed by FACS analysis. Infection of DCs was uniformly 40-60%.

Expression and Purification of Recombinant EBNA-1 and PCNA Control Protein.

$EBNA-1_{458-641}$ was inserted in the expression vector pET15b (Novagen, Madison, Wis.). The vector was transfected into E. coli BL21 (DE3) pLysS cells. Proliferating cell nuclear antigen (PCNA) was expressed in E. coli BL21 (DE3) pLysS cells (gift from Ming Guo, Cornell University Medical College, New York). Bacterial cultures were grown to an $OD_{595}$ of 0.8 at 37° C. Then EBNA-1 or PCNA expression was induced with 1 mM IPTG (GibcoBRL, Grand Island, N.Y.) for 3 hours. After harvesting by centrifugation, the cells were resuspended in 50 mM $NaH_2PO_4$, 300 mM NaCl and 10 mM imidazole to a volume of 5 ml/g cell pellet. Lysozyme was added to 1 mg/ml for 30 minutes on ice, and the suspension was sonicated for complete lysis. After centrifugation at 20,000×g for 30 minutes at 4° C., the cleared supernatant was filtered through a 0.45 μm filter and 1 ml of Ni-NTA Agarose (Qiagen, Valencio, Calif.)/10 ml lysate was added. The suspension was rotated for 1 hour at 4° C. and packed into a column (Biorad, Hercules, Calif.). The matrix was washed with 50 mM $NaH_2PO_4$, 300 mM NaCl and 20 mM imidazole until the flow through $OD_{280}$ was <0.01. The recombinant proteins were then eluted with 50 mM $NaH_2PO_4$, 300 mM NaCl and 250 mM imidazole. Protein containing fractions were pooled and dialyzed overnight at 4° C. against PBS. The protein concentration was determined at $OD_{280}$, purity was determined by SDS PAGE, and identity determined by Western blot with EBNA-1-specific antibody (MAB8173) (CHEMICON Internat. Inc., Temecula, Calif.) or the 6×H specific antibody AD1.1.10 (R&D Systems).

ELISPOT Assay for IFNγ and IL-4 Secreting Cells.

ELISPOT assays were performed as described above. A vvEBNA-1ΔGA response was considered significant if it were 10 spots greater than the negative control (vvTK−) and at least twice that of the negative control.

Expansion of EBNA-1-Specific ELISPOT Producing, CD4+ T Cells.

Positively-selected CD4+ T cells were expanded for 7 days, in medium supplemented with 5% PHS, with vvEBNA-1ΔGA-infected DCs or vvTK-infected DCs at a DC: T cell ratio of 1:30. In some experiments 5 μg/ml of W6/32 anti-MHC class I or L243 anti-MHC class II blocking antibody was added on day 0, 3 and 7. At day 7, expanded cells were restimulated with DCs pulsed with 1 μg/ml rEBNA-1 or control protein, rPCNA, and assayed for IFNγ or IL-4 ELISPOTs. In other experiments, the vaccinia expanded T cells were restimulated with DCs pulsed with the indicated doses of either rEBNA-1 protein or PCNA control protein on day 7.

Generation of EBNA-1-Specific Cell Lines by Cytokine Secretion in Freshly Stimulated PBMC.

$75 \times 10^6$ PBMCs were stimulated with autologous vvEBNA-1ΔGA-infected DCs at a ratio of 30:1 in medium fortified with 5% PHS for either 7 hours (IFNγ) or 18 hours (IL-4). Then the cells were washed with MACS buffer, centrifuged for 10 minutes at 1800 rpm, and resuspended in cold RPMI containing 10% fetal calf serum (R10) at a concentration of $10^7$ cells/80 μl of media. A primary anti-CD45 antibody, conjugated to either anti-IFNγ or anti-IL-4 (Miltenyi), was then added at a ratio of 10 μl of antibody per $10^7$ cells. The cells were then placed on ice for 5 minutes, followed by the addition of warm R10 to a concentration of $5 \times 10^6$ cells/ml, and incubated for 45 minutes under continuous rotation at 37° C. Following this incubation, cells were washed with MACS buffer and centrifuged. The pellet was resuspended in 80 μl of MACS buffer/$10^7$ cells and 10 μl of secondary antibody to either IFNγ or IL-4 labeled with PE (Miltenyi) was added per $10^7$ cells. The cells were placed on ice for 10 minutes, and then washed with MACS buffer and centrifugation. A final anti-PE antibody labeled with a paramagnetic microbead (Miltenyi) was added at a ratio of 10 μl/$10^7$ cells for 15 minutes at 4° C. Magnetic separation was performed as above and repeated to increase purity of the recovered cells. The cells were then centrifuged and cultured in medium with 5% PHS and $10^5$ irradiated CD14− feeder cells in one well of a 96 well plate. The cells were restimulated weekly; alternating vvEBNA-1ΔGA-infected DCs with DCs pulsed with 2 μg/ml rEBNA-1 at the time of the maturation stimulus (day 5-7). After 3 weeks, 10 U/ml IL-2 (Lymphocult, Biotest, Minneapolis, Minn.) was added. In this way, we were able to set up lines from cells in fresh blood that secreted IFNγ and IL-4 in response to EBNA-1-pulsed DCs.

FACS and Functional Analysis of IFNγ and IL-4 Cell Lines.

3 weeks after initiation of the lines as above, $10^4$ cells were stained for 15 minutes on ice with Simultest (CD4 and CD8, BD PharMingen, San Diego, Calif.) at 1:50 or with PE-labeled CD56 antibody (Becton-Dickenson). After 3 washes and fixation with 4% paraformaldehyde, cells were analyzed on a FACScan (Becton-Dickenson). For cytotoxic activity, the cell lines in triplicate were added to $10^4$ targets at the indicated effector: target ratios for 5 hours or 24 hours. The targets were labeled with 50 μCi $Na_2^{51}CrO_4$ for 1 hour at 37° C., and washed 3 times with R10. To measure cytolysis, 50 μl of culture supernatant was added to 100 μl of scintillation fluid (Wallac, Finland) in a 96-well sample plate, and radioactivity measured in a γ counter (1450 Microbeta counter, Wallac). Percent specific lysis was calculated by the following formula: ([cpm experimental well-cpm spontaneous release]/[cpm total release-cpm spontaneous release])× 100%. Spontaneous release was determined by incubating labeled targets in medium alone; total release was determined by incubating targets with 1% Triton X-100.

ELISA for IgG Subclasses.

96 well polystyrene plates (Nunc, Rochester, N.Y.) were coated with 1 µg/well of rEBNA-1 protein, mumps skin antigen USP (Pasteur Merieux Connaught, Swiftwater, Pa.), tetanus toxoid (Lederle, Philadelphia, Pa.), *candida albicans* cell lysate (Allermed Lab, San Diego, Calif.) in PBS or with PBS alone overnight at 4° C. Plates were blocked with 50 µl/well 3% non-fat milk powder for 30 minutes followed by 30 minutes in PBS containing 3% BSA. Test plasma samples, diluted 1:10 or 1:100 in 3% BSA, were added for 20 minutes at RT. Plates were washed 3 times with TBST (10 mM Tris, 140 mM NaCl, 0.05% Tween 20). Biotin-mouse anti-human IgG1, IgG2, IgG3, IgG4 antibodies (PharMingen) were added at 1:1000 for 20 minutes at RT. Plates were washed 3 times in TBST, avidin-bound biotinylated HRP was added for 20 minutes at RT, followed by TMB substrate (R&D systems) to develop the reaction for 10 minutes at RT and 1M $H_2(SO_4)$ to stop the reaction, and the plates were read in a microplate reader (Dynex, Chantilly, Va.).

Results

CD4+ T Cell Responses to EBNA-1 in Cultured PBMCs Primarily Involve IFNγ $T_H1$ Cells.

Figure 7A:
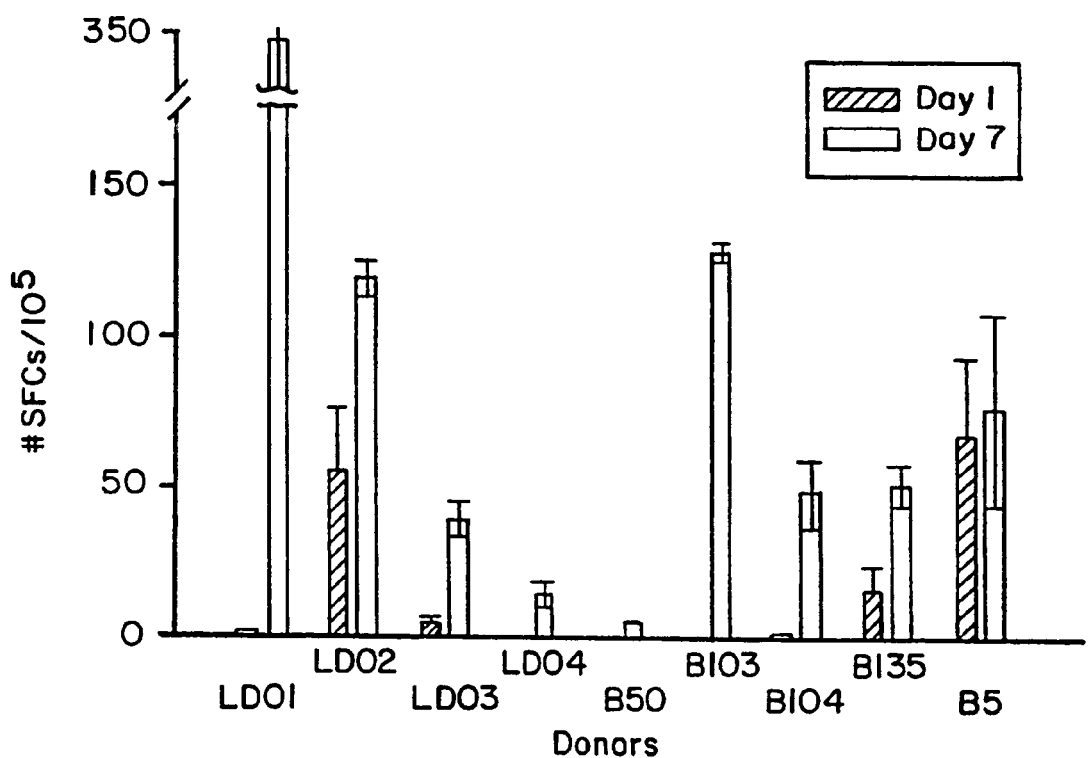
FIGS. 7A and 7B. EBNA-1-specific T cell responses are dominated by $T_H1$ cytokine secretion. CD4+ T cells were stimulated with dendritic cells infected with vvEBNA-1ΔGA or vvTK− (negative control) and tested for their secretion of IFN-γ (A) or IL-4 (B) on the day of T cell isolation (day 1) and after one week expansion (day 7). Values shown are the mean of triplicates and were derived by the subtraction of the negative control from the number of EBNA-1-specific spots. The values of the vvTK− control ranged from 0 to 105. A vvEBNA-1ΔGA response was considered significant if it were at least ten spots above vvTK− negative control and at least twice that of the negative control.

In Example 1, we identified EBNA-1-specific, IFNγ-secreting, CD4+ T cells using two, week-long stimulations by DCs infected with recombinant vaccinia EBNA-1 virus (vvEBNA-1ΔGA). Here, we assessed if this response could be detected in 1 day and 1 week cultures, and we enumerated both IFNγ and IL-4 secreting cells. At both time points, no EBNA-1-dependent T cells could be detected in cultures stimulated with DCs infected with control vaccinia virus (vvTK−). With DCs expressing vvEBNA-1ΔGA, we found $T_H1$ cells in 3/9 normal donors after 1 day of culture, but did not find $T_H2$ cells in any donors (FIGS. 7A, B). In 1 week cultures, 8/9 donors demonstrated an expansion of IFNγ cells, but only 1/9 had EBNA-1 dependent IL-4 secretors (FIGS. 7A, B). In the one IL-4 secretor, the number of IFNγ ELISPOTS was three times greater than the IL-4 ELISPOTS. Therefore, in most donors, EBNA-1 responsive CD4+ T cells have a $T_H1$ phenotype, secreting IFNγ and not IL-4. This is a surprising and unexpected result considering that others have found the EBNA-1-specific T cell response is $T_H2$ in phenotype, rather than $T_H1$ (see, Steigerwald-Mullen, et al., J. Virol., 2000, 74:6748-6759).

To verify that these CD4+ T cell responses were MHC class II restricted, we stimulated T cells with vvEBNA-1ΔGA-infected DCs for one week in the absence or presence of blocking antibodies to MHC Class I (W6/32) or HLA-DR (L243). When IFNγ-secreting cells were enumerated by ELISPOT, only the L243 monoclonal antibody decreased responses, by a range of 88-100% in 3 experiments. We conclude that CD4+ T cell responses to EBNA-1 are primarily MHC II restricted and of the $T_H1$ type.

Figure 7B:
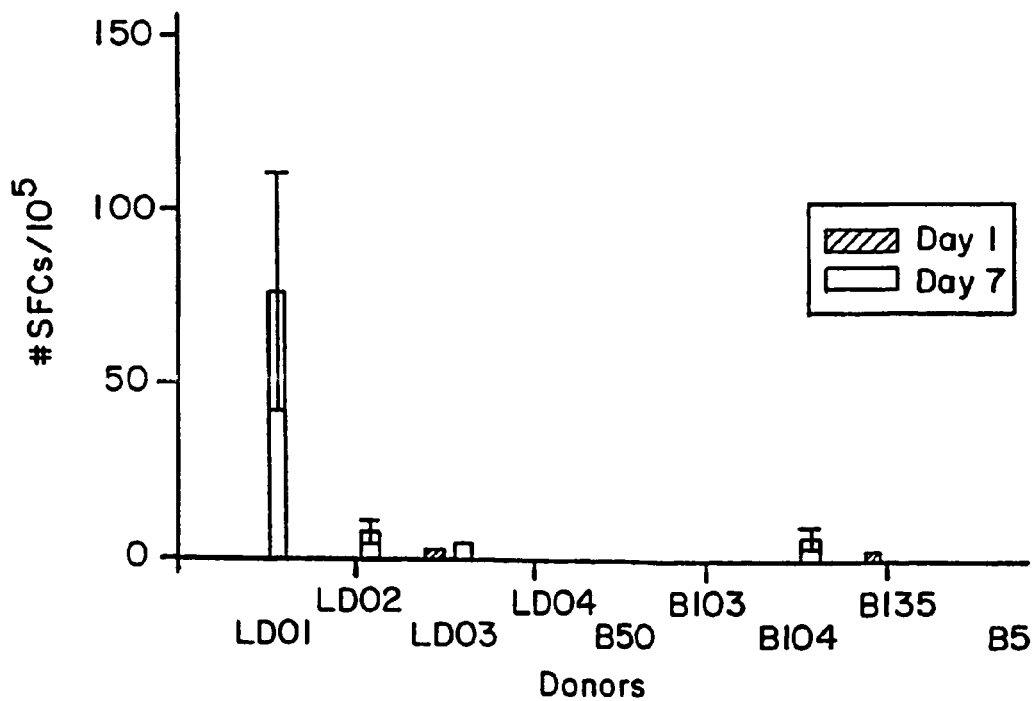
Figure 8A:
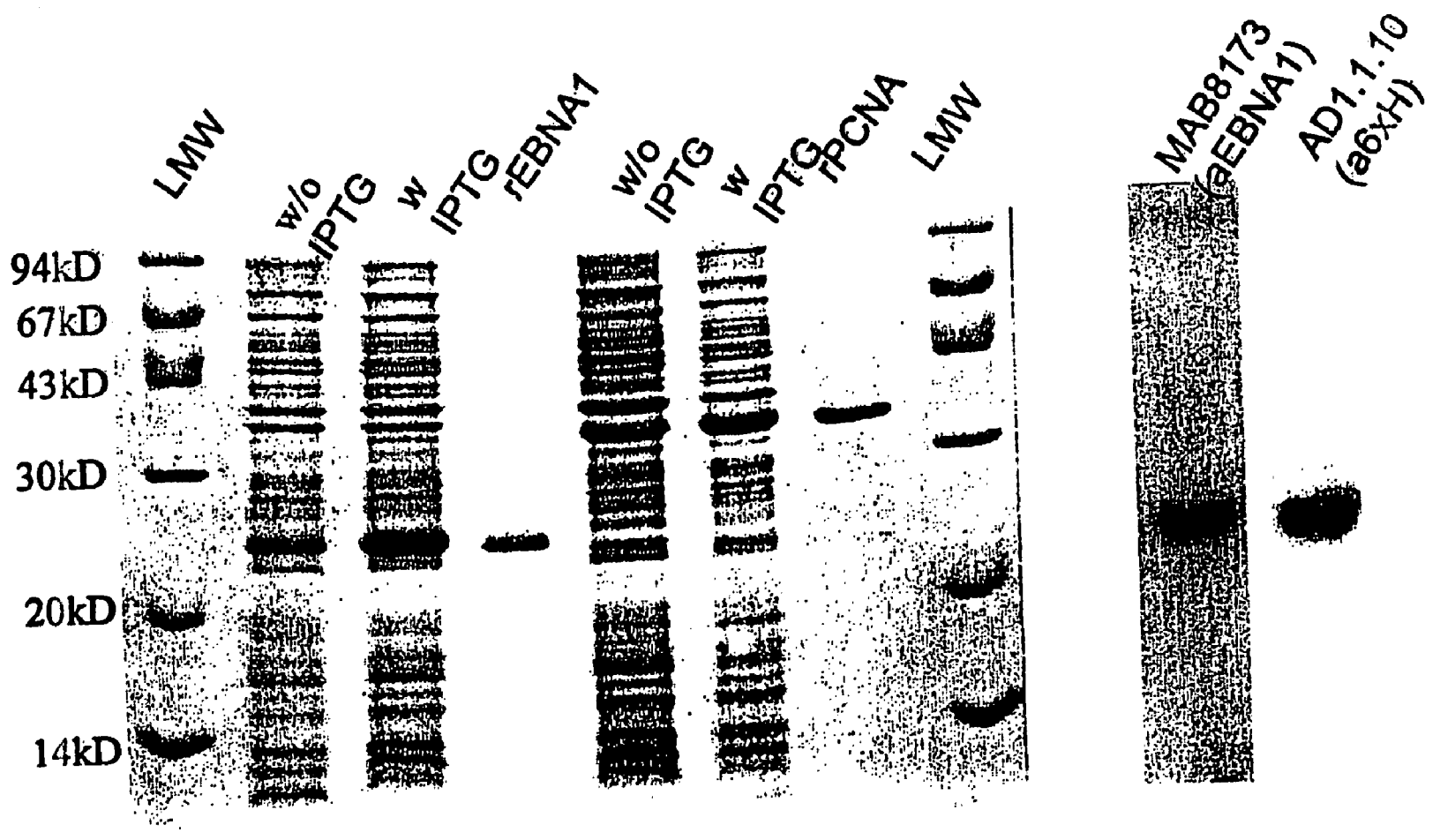
Figure 8B:
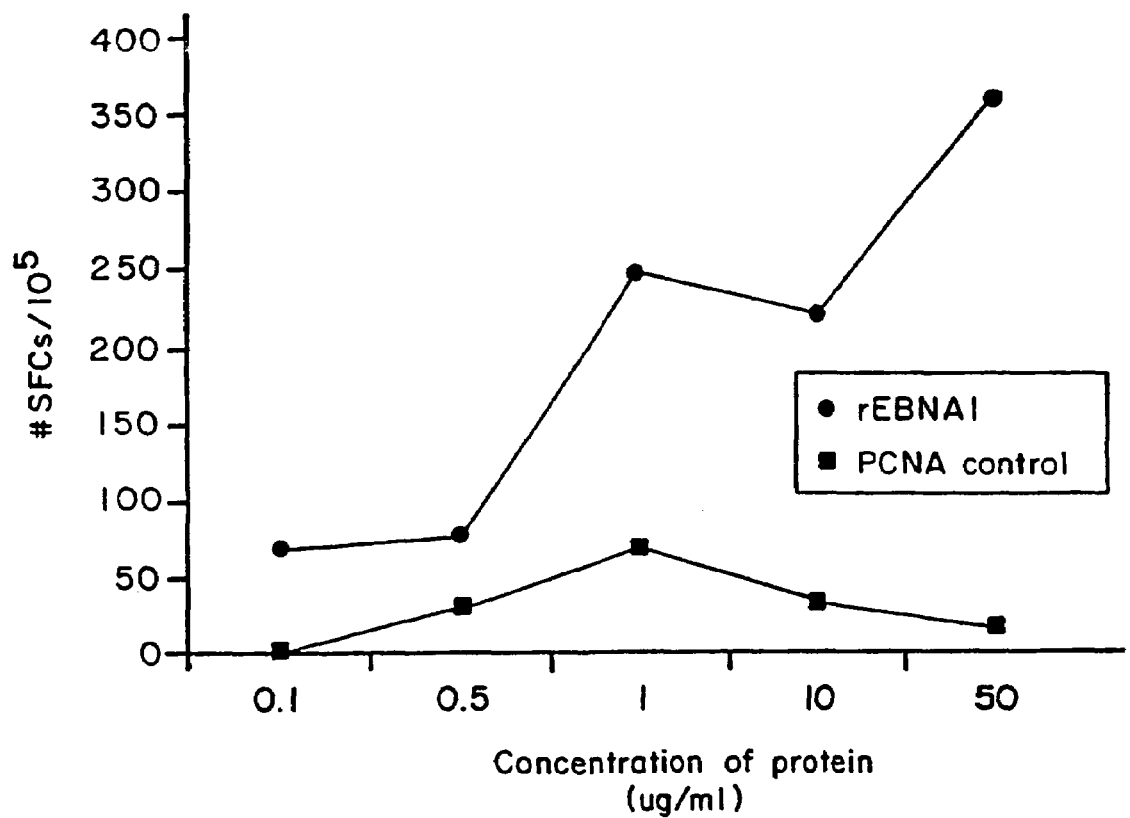
FIGS. 8A and 8B. EBNA-1-specific responses can be detected at very low doses of antigen. A recombinant EBNA-1 protein or control proliferating cell nuclear antigen (PCNA) protein was eluted from E. coli expressing vectors. A. Proteins were dialyzed overnight and tested for purity with SDS PAGE. The recovered rEBNA-1 protein was tested for specificity by Western blot using an anti-EBNA-1 antibody MAB8173. The antibody AD1.1.10 recognizes a histidine tag which is contained in the rEBNA-1 protein. B. vvEBNA-1ΔGA-infected DCs were used to expand CD4+ T cells in a one week culture. The expanded T cells were restimulated using DCs pulsed with the indicated concentration of rEBNA-1 protein or rPCNA control protein and read-out with ELISPOT. The rEBNA-1 protein was added to the DCs during the maturation phase (day 6-8) of the DC culture. The inset graph shows the ELISPOT results of CD4+ T cells expanded with vvEBNA-1ΔGA-infected DCs for one week and restimulated with either vvEBNA-1ΔGA-infected DCs or vvTK− control.
Figure 8C:
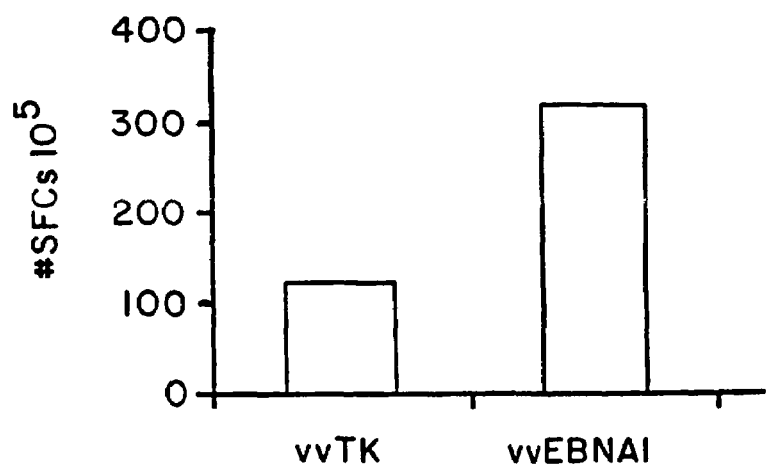
Figure 9A:
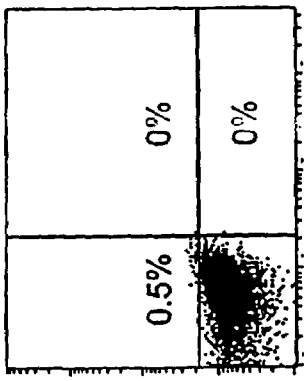
FIGS. 9A, 9B, 9C, 9D, 9E, and 9F. EBNA-1-specific cells from fresh blood are CD4+ T cells. Freshly isolated PBMCs were stimulated with vvEBNA-1ΔGA-infected dendritic cells for either 7 hours for maximal production of IFNγ, or 18 hours for IL-4. They were then positively selected based on the secretion of either IFNγ or IL-4. IFNγ cell lines were established in 6/6 donors and IL-4 cell lines in 3/6 donors. Shown are control stains (A,B,C) CD4 and CD8 stains (D, E, F) of three IFNγ lines analyzed by FACS. The gates were set on the lymphocyte population and on living cells as determined by propidium iodide staining.
Figure 9B:
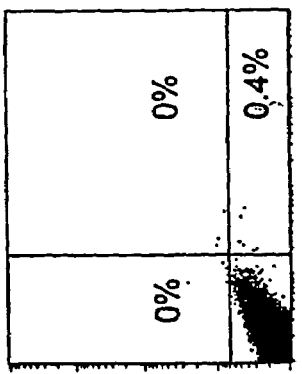
Figure 9C:
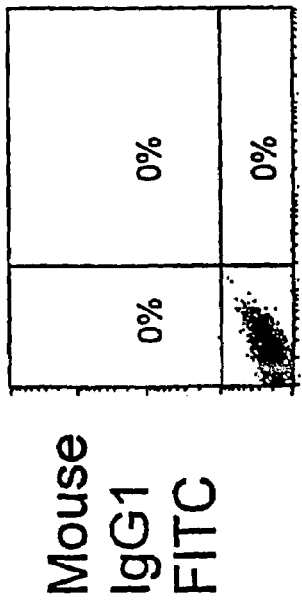
Figure 9D:
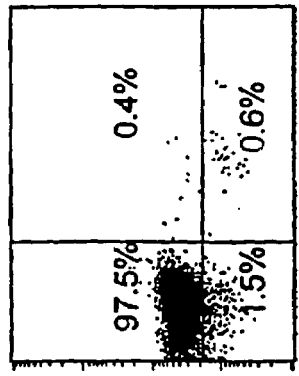
Figure 9E:
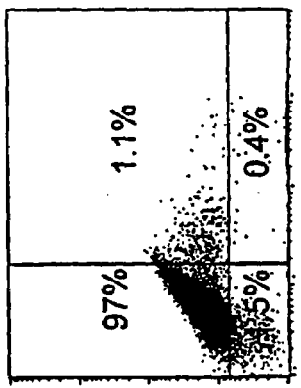
Figure 9F:
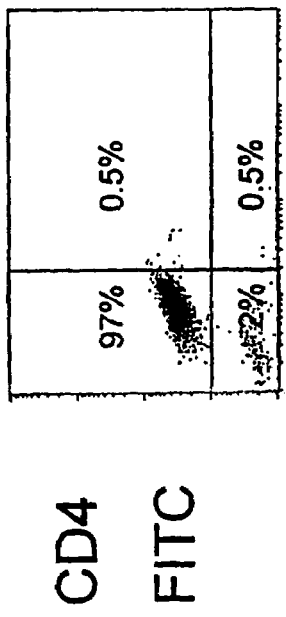

The experiments in FIG. 7 used vaccinia vectors both to expand the EBNA-1-specific cells for one week and for restimulation in the ELISPOT assay for one day. Therefore, we then tested the efficacy of purified EBNA-1 protein as antigen in the ELISPOT assay. A recombinant EBNA-1 protein consisting of the amino acids 458-641 of the EBNA-1 sequence or rPCNA, as a control protein, were extracted from transformed *E. coli* cultures after IPTG induction. The extract was dialyzed overnight against PBS and was checked for purity and specificity by SDS PAGE and Western blot (FIG. 8A). These proteins were pulsed onto DCs in varying concentrations and used to read-out IFNγ ELISPOTs after a one week expansion using vvEBNA-1ΔGA-infected DCs. FIG. 8B shows the dose response curve seen with the titration of rEBNA-1 protein as compared to the PCNA control. The graph in FIG. 8C compares the response of vvEBNA-1ΔA expanded cells restimulated with vvTK− or vvEBNA-1ΔGA. A dosage of only 1 µg/ml of rEBNA-1 protein pulsed onto DCs gives a response that is comparable to that of the recombinant vaccinia EBNA-1. This result demonstrates that EBNA-1-specific $T_H1$ cells are capable of responding to very low doses of EBNA-1.

EBNA-1-Specific, Cytokine-Secreting Cells Isolated Directly ex Vivo are Primarily CD4+.

Since the EBNA-1-specific ELISPOT responses from most donors required a week's culture of CD4+ T cells with DCs, which make high levels of the TH1 skewing cytokine IL-12 (Cella, et al., J. Exp. Med., 1996, 184:747-752; Koch, et al., J. Exp. Med., 1996, 184:741-746), we isolated EBNA-1-specific cells directly ex vivo. Fresh PBMCs from 6 donors were stimulated for 7 hours (IFNγ) or 18 hours (IL-4) with vvEBNA-1ΔGA-infected DCs. Then the cells were labeled with anti-CD45 antibody conjugated to either anti-IFNγ or IL-4 antibody. In this way, cells that were secreting cytokine would capture a second antibody specific to another epitope of IFNγ or IL-4, labeled with PE. A final anti-PE antibody conjugated to a magnetic microbead was added and the cells selected in a magnetic field. The recovered cells were expanded by weekly restimulations, alternating vvEBNA-1ΔGA-infected DCs with DCs pulsed with rEBNA-1 protein.

EBNA-1-specific, IFNγ secreting cell lines were established in all 6 donors, and IL-4 secreting lines in 3/6 donors. When the lines were analyzed by FACS (for CD56, CD4 or CD8), both IFNγ and IL-4 lines consisted primarily of CD4+ cells. FIG. 9 shows IFNγ secreting lines from 3 donors, i.e., >90% of the cells expressed CD4 and <2% CD8 or CD56 (data not shown). Likewise three EBNA-1-specific, IL-4 secreting lines consisted of >90% CD4 and <2% CD8 or CD56 cells (data not shown). We conclude that EBNA-1-specific, cytokine-secreting CD4+ T cells in healthy adults are already differentiated in vivo (FIG. 9), but these cells typically must be expanded for 1 week with autologous DCs in vitro to be detected in ELISPOT assays (FIG. 7).

EBNA-1-specific $T_H1$ and Not $T_H2$ CD4 T Cells are Able to Lyse EBNA-1-Expressing DCs.

Figure 10A:
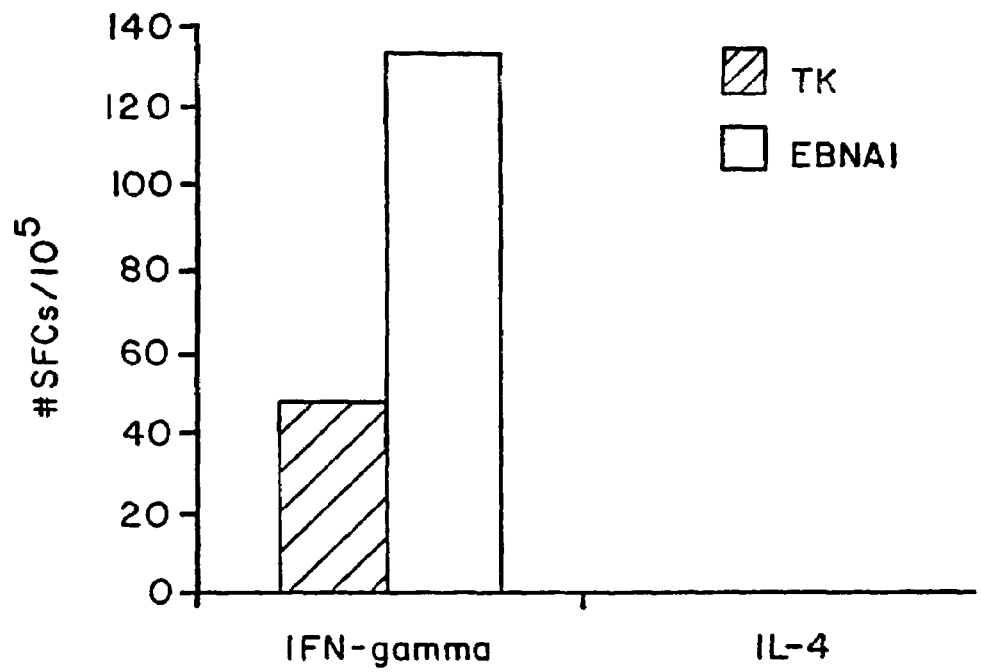
FIGS. 10A, 10B, 10C, 10D, and 10E. EBNA-1-specific $T_H1$ cells and not $T_H^2$ cells lyse EBNA-1-expressing DCs.
Figure 10B:
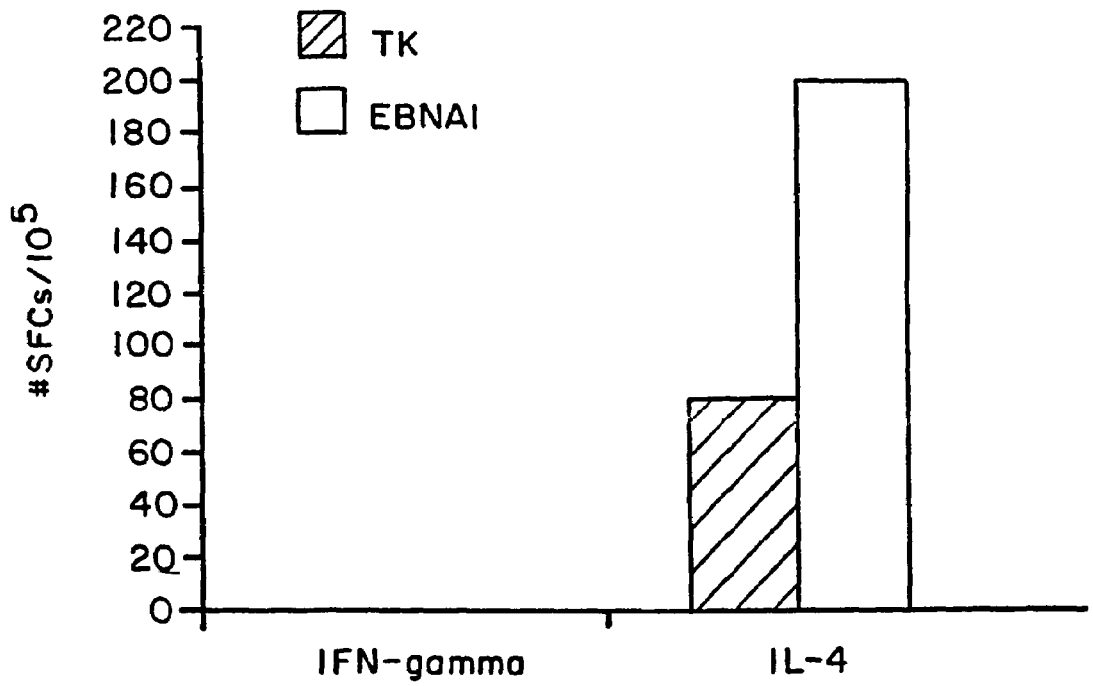
Figure 10C:
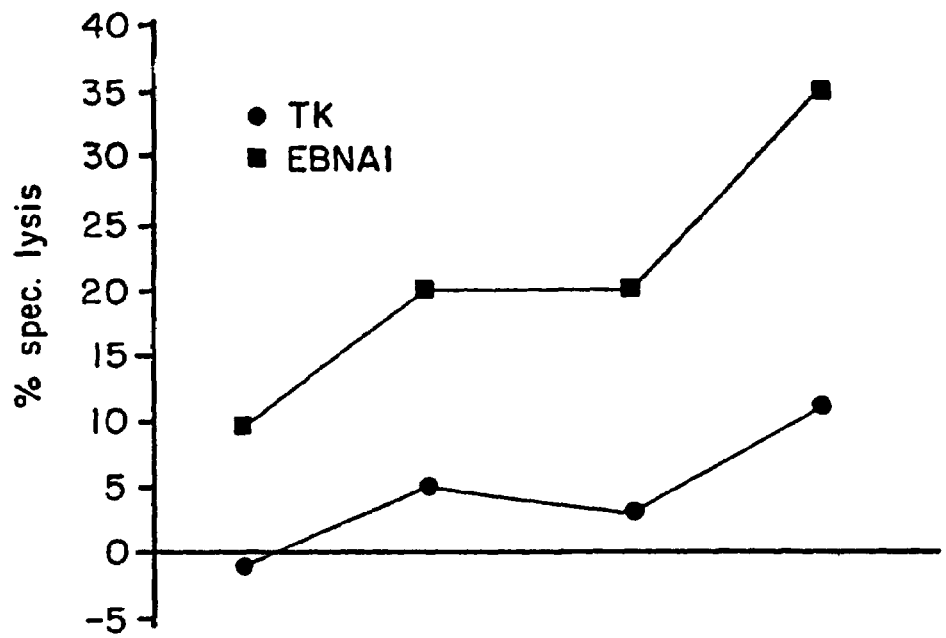
Figure 10D:
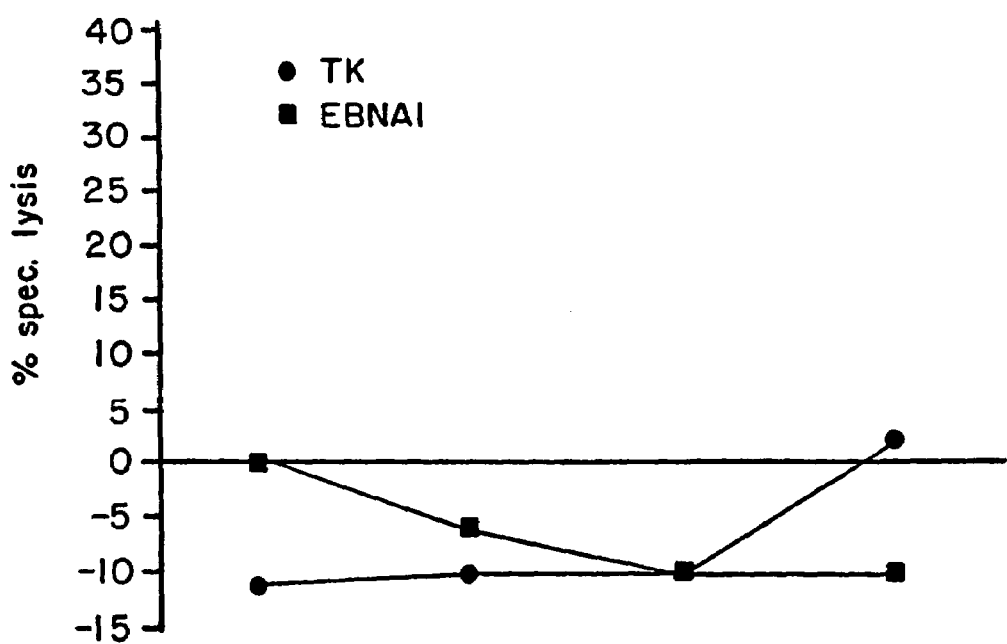
Figure 10E:
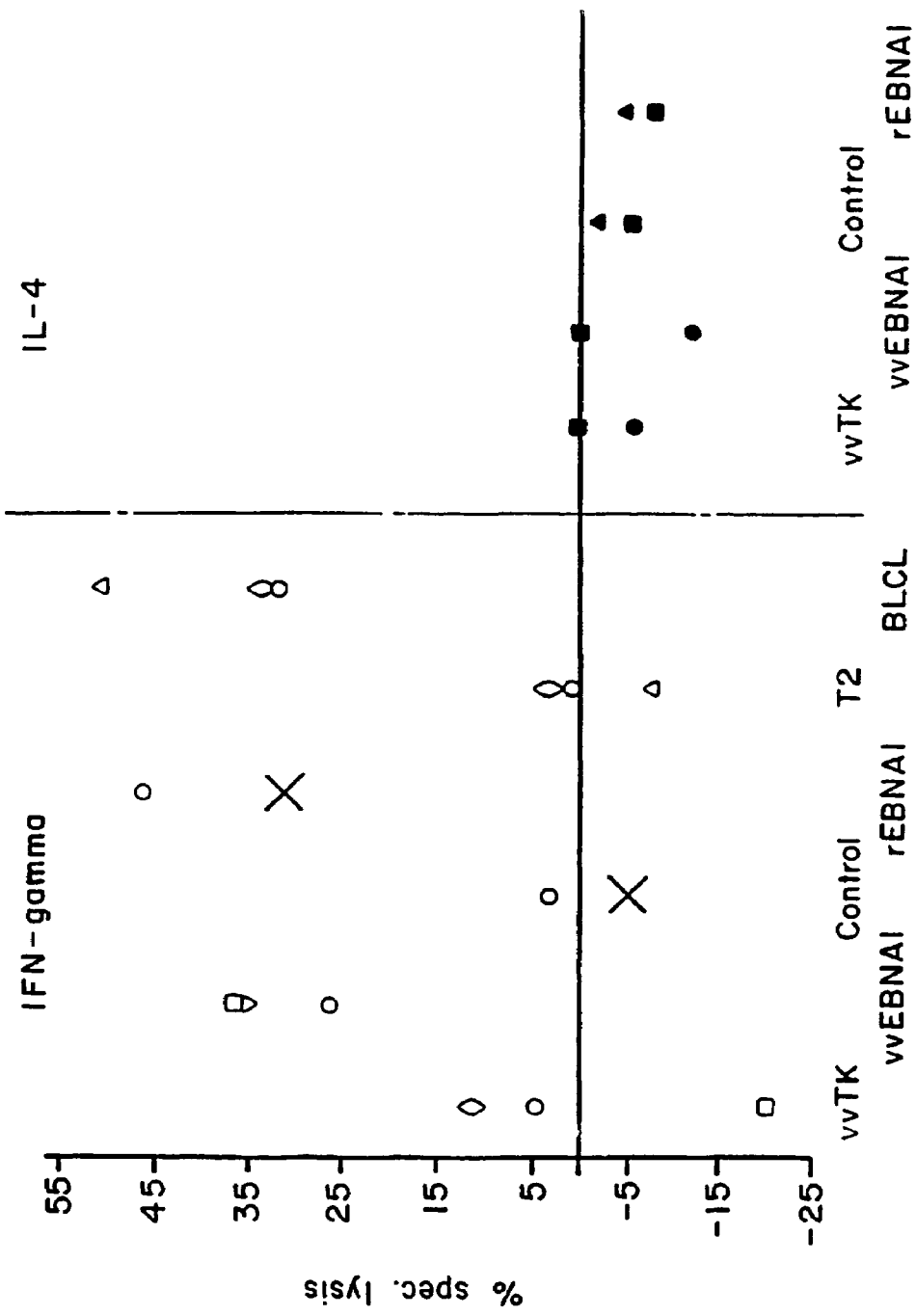
Figure 11A:
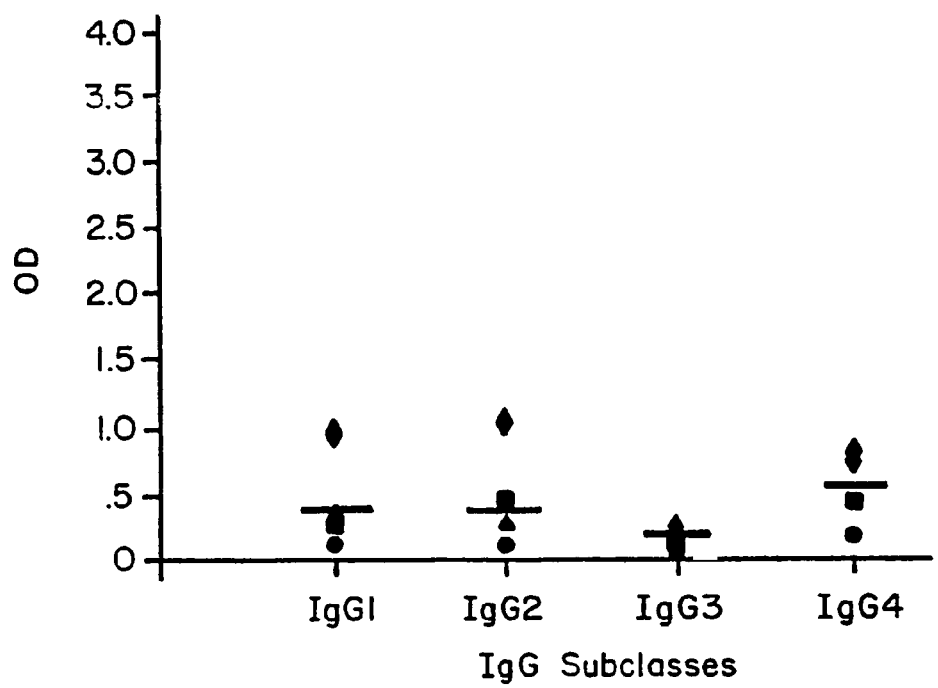
Figure 11B:
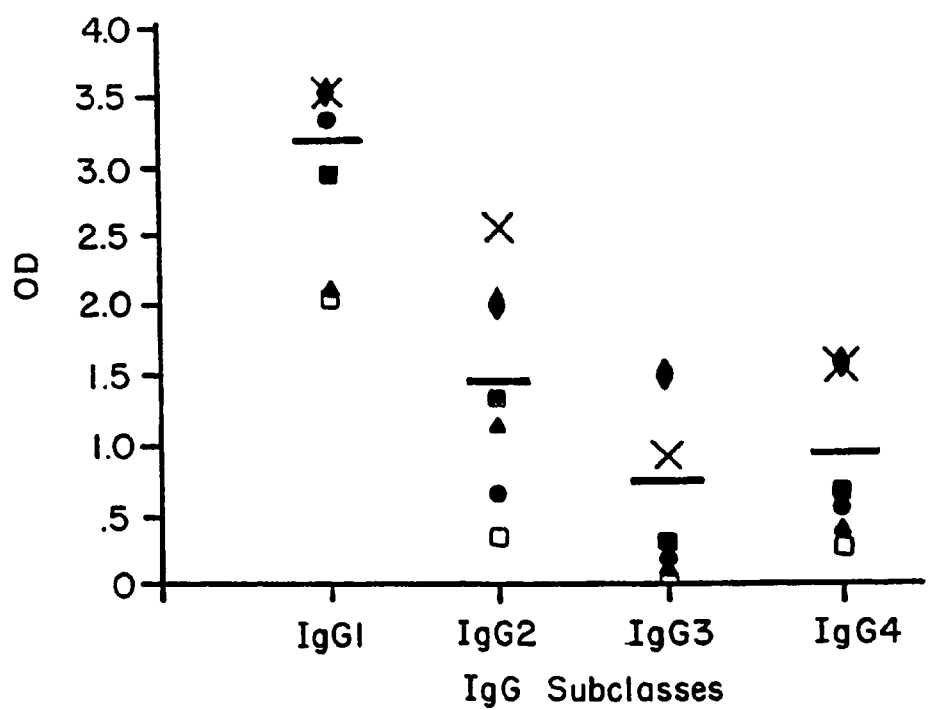
Figure 11C:
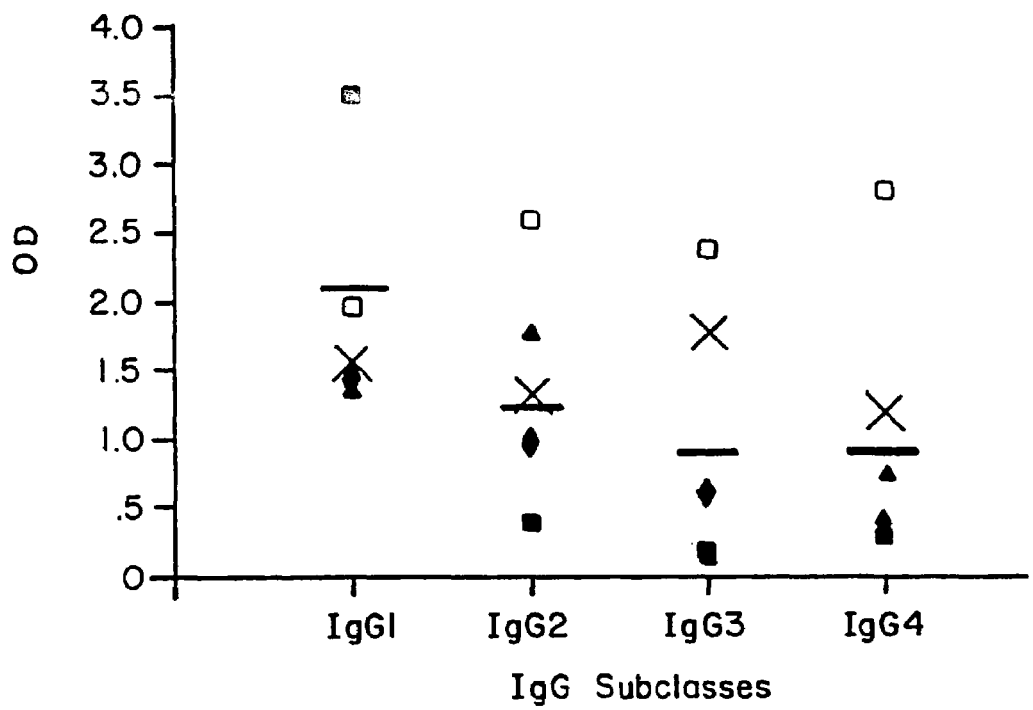
Figure 11D:
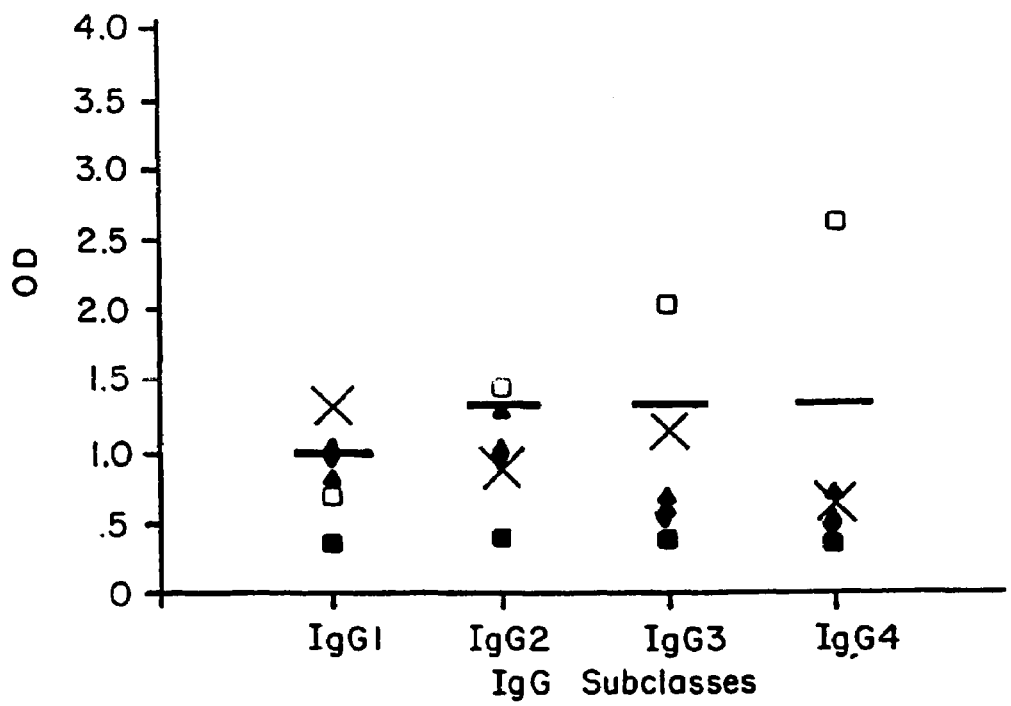
Figure 11E:
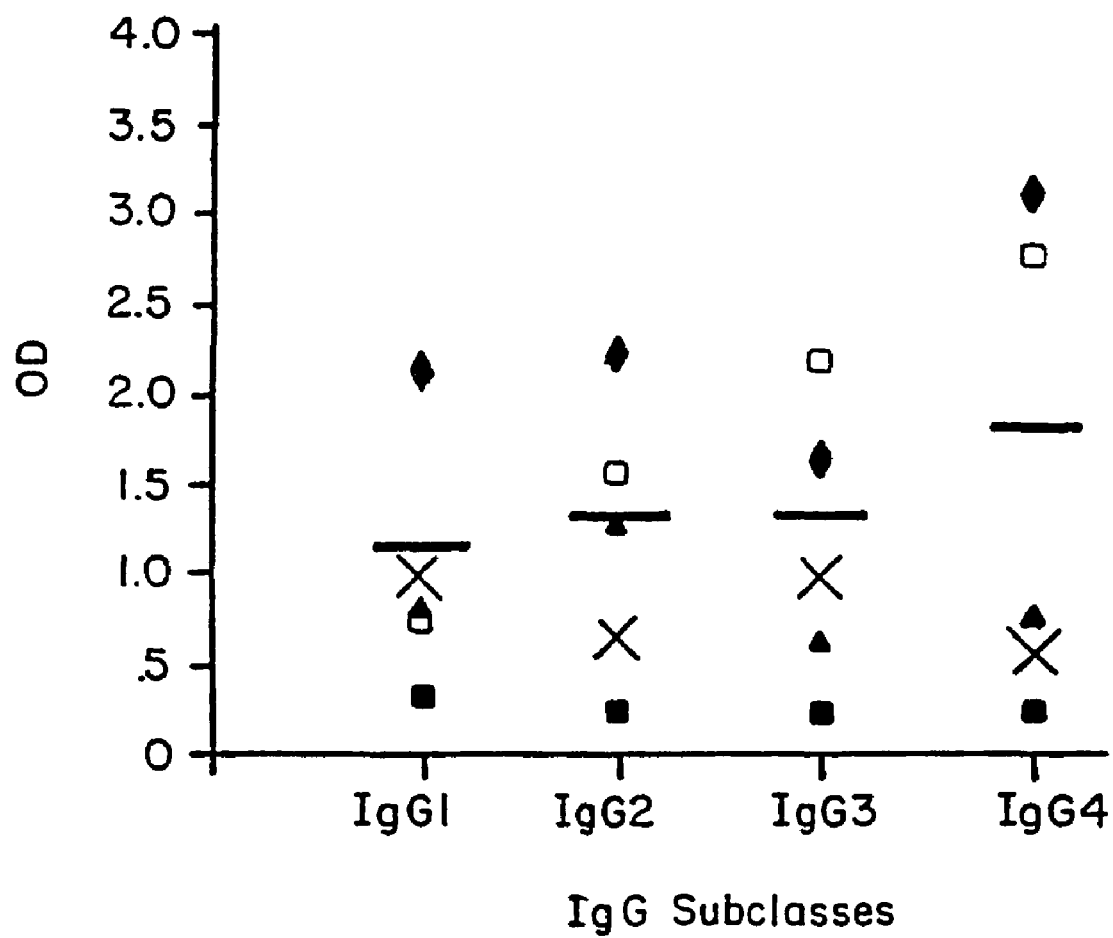

We have shown that EBNA-1-specific T cell lines can kill autologous B-LCL and DCs pulsed with different sources of EBNA-1 protein. We assessed if this function was primarily expressed by $T_H1$ lines, as has been observed with CD4+ T cells specific for other antigens (Erb, et al., Cell Immunol., 1991, 135:232-44; Erb, et al., J. Immunol., 1990, 144:790-795; Del Prete, et al., J. Exp. Med., 1991, 174:809-13; Nishimura, et al., J. Exp. Med., 1999, 190:617-628). IFNγ cell lines from 5 donors and IL-4 lines from 3 donors were studied simultaneously in cytotoxicity and ELISPOT assays. The cell lines, which had been isolated from fresh PBMCs on the basis of EBNA-1 dependent, IFNγ or IL-4 production, maintained a $T_H1$ or $T_H2$ polarity after weeks of stimulation in the absence of exogenous IL-12 or IL-4 (FIGS. 10A, B). When we tested lysis of vvEBNA-1ΔA-infected DCs, DCs loaded with rEBNA-1 protein or autologous B-LCL by $^{51}Cr$ release assay, only $T_H1$ lines lysed EBNA-1-expressing targets over the controls, though the $T_H2$ cell lines recognized EBNA-1-expressing DCs with the secretion of IL-4. FIGS. 10C, D shows this data at graded effector:target ratios, while FIG. 10E summarizes killing at an E:T ratio of 10:1 for several lines. $T_H1$ but not $T_H2$ cell lines had cytolytic activity (FIG. 10E).

EBNA-1-Specific IgG Subclasses in Vivo Reflect $T_H1$ Immunity.

To assess the relative activity of EBNA-1 specific $T_H1$ and $T_H2$ cells in vivo, we monitored the IgG subclass of the antibody response. $T_H1$ cytokines skew antibody responses towards the IgG1 isotype, and $T_H2$ toward IgG4, although the IgG subclass distribution in humans may not be as strictly biased as described for mice (Bonifacio, et al., J. Immunol., 1999, 163:525-32; Sousa, et al., Clin. Exp. Immunol., 1998, 111:48-55; Hussain, et al., Immunology., 1999, 98:238-43). An ELISA assay for IgG subclasses was used to describe the isotype of EBNA-1-specific IgG antibodies in 7 donors. As antigen, we used either a commercially-available gly-ala repeat sequence from EBNA-1, or the C-terminal rEBNA-1 protein expressed by E. coli vectors. All 7 donors showed a clear predominance of IgG1 antibodies in their EBNA-1 response (FIG. 11). This contrasts to responses to the three other antigens that we tested (mumps skin antigen, tetanus toxoid and candida lysate; FIG. 11), although two donors did make a strong IgG1 response to tetanus toxoid. The antibody data, coupled with the ready detection of IFNγ secreting T cells in fresh and 1 week cultures of PBMC, indicates that the response to EBNA-1 in vivo in healthy EBV carriers is consistently $T_H1$ in type.

Discussion

The new data indicate that healthy EBV carriers consistently make a $T_H1$ type response to EBNA-1 in vivo. These T cells are present in the blood and likely account for the unambiguous skewing of EBNA-1 antibody responses to the IgG1 isotype (FIG. 10). Since B cells and B cell lines are not known to actively produce IL-12, or to bias the CD4+ T cell response towards $T_H1$, we suspect that DCs are responsible for skewing T cells in this fashion. It is now known that human DCs efficiently process EBNA-1 from dying EBV-infected B cells (Münz, et al., J. Exp. Med., 2000, 191:1649-60), and that mouse DCs skew T cells towards the $T_H1$ type in vivo (Pulendran, et al., Proc. Natl. Acad. Sci. USA, 1999, 96:1036-1041; Maldonado-Lopez, et al., J. Exp. Med., 1999, 189:587-592). If human B cells have to undergo a lytic infection to enable DCs to present EBNA-1 in vivo, one would expect a delay in the development of EBNA-1-specific antibodies, as is typical of EBV infection (Rickinson, and Kieff, Epstein-Barr Virus. In Virology. B. N. Fields, D. M. Knipe, and P. M. Howley, editors. 1996, Lippincott-Raven, Philadelphia. 2397-2446). Therefore, we suggest that the $T_H1$ response to EBNA-1 reflects a dominant role for DCs relative to infected B cells, as the direct inducers of EBNA-1 immunity.

CD4+ T cells are important in resistance to virus infections and tumors. In HIV-1 infection, strong CD4+ T cell responses are found in long term nonprogressors (Rosenberg, et al., Science, 1997, 278:1447-1450). This minority of HIV-infected patients have high CD4+ T cell counts and low viral loads without anti-retroviral therapy. They also display more vigorous CD4+ T cell proliferative responses to HIV p24 and gp160 protein. The role of CD4+ T cells in chronic viral infection has been more directly assessed in mice (Cardin, et al., J. Exp. Med., 1996, 184:863-871). Primary infection with the murine MHV-68 γ-herpesvirus resolves similarly in MHC class II$^{-/-}$ and $^{+/+}$ mice. However, 3 weeks after the initial infection, the virus recrudesces in MHC II knock-out mice which then develop wasting and within 4 months, the majority of the mice die. This occurs in spite of the fact that initial viral clearance takes place, apparently through CD8+ T cell cytotoxicity. Analogous findings have been made in studies of CD8+ effector function towards LCMV infection in CD4$^{-/-}$ and wild type mice (Zajac, et al., J. Exp. Med., 1998, 188:2205-2213). The CD4$^{-/-}$ mice fail to eliminate an LCMV variant that causes more widespread and chronic infection, and the variant-specific CD8+ T lymphocytes are non-functional (as measured by IFNγ secretion), despite expression of lymphocyte activation markers. Together these results are part of an emerging consensus that CD4+ T cells maintain effective CD8+ T cell function against viruses (reviewed in Kalams and Walker, J. Exp. Med., 1998, 188:2199-2204) and tumors (reviewed in Toes, et al., J. Exp. Med., 1999, 189:753-756).

The mechanism underlying this role for CD4+ T cells likely entails improved function of antigen presenting cells, especially DCs (Schoenberger, et al., Nature, 1998, 393:480-483; Ridge, et al., Nature, 1998, 393:474-478; Bennett, et al., Nature, 1998, 393:478-480). The DCs, following interaction with CD4+ T cells, become more effective stimulators of CD8+ T cells, both in their initial expansion and maintenance. CD40L, which is expressed more abundantly on activated CD4+ than CD8+ T cells, is strongly implicated as the stimulus for DCs. CD40 is abundant on DCs, and its ligation mediates several critical steps in DC development and function. This includes their generation from CD34+ progenitors (Flores-Romo, et al., J. Exp. Med., 1997, 185:341-349), mobilization from peripheral tissues (Moodycliffe, et al., J. Exp. Med., 2000, 191:2011-20), maturation (Caux, et al., J. Exp. Med., 1994, 180:1263-1272), survival (Josien, et al., J. Exp. Med., 2000, 191:495-501), and cytokine secretion, particularly IL-12 (Cella, et al., J. Exp. Med., 1996, 184:747-752; Koch, et al., J. Exp. Med., 1996, 184:741-746).

$T_H1$ are more important than $T_H2$ CD4+ cells in resistance to viruses and tumors. In humans, it has been proposed that $T_H1$ CD4+ T lymphocytes resist primary CMV infection in renal transplant recipients (Rentenaar, et al., J. Clin. Invest., 2000, 105:541-8). CMV seronegative recipients of CMV-positive kidneys were monitored for CMV-specific immune responses after transplantation. In all patients evaluated, a polarized $T_H1$ response was observed. These patients recovered from acute infection without signs of chronic CMV disease, despite immunosuppressive therapy. Furthermore, studies of mouse models emphasize the importance of $T_H1$ CD4+ cells in immunological resistance. When ovalbumin was expressed in tumors as a surrogate antigen, adoptive transfer of ovalbumin-specific $T_H1$ cells led to stronger CD8+ T cell memory than adoptive transfer of $T_H2$ cells with the identical T cell receptor for the antigen (Nishimura, et al., 1999, supra). Neonatal mice immunized with an influenza subunit vaccine in combination with IL-12 exhibited enhanced $T_H1$ cytokine expression and demonstrated 100% survival after challenge with influenza virus in comparison to a 55% survival rate among neonatal mice immunized with the influenza subunit vaccine alone (Arulanandam, et al., J. Immunol., 2000, 164:3698-704). A recent study employed adoptive transfer into TCRβ$^{-/-}$δ$^{-/-}$ mice of $T_H1$ and $T_H2$ cells expressing an identical TCR transgene specific for the vesicular stomatitis virus (VSV) glycoprotein (Maloy, et al., J. Exp. Med., 2000, 191:2159-70). Both $T_H1$ and $T_H2$ T cells conferred systemic protection against VSV infection, most likely through the elaboration of neutralizing antibodies. However, only the $T_H1$ CD4+ T cells were able to protect against lethal intranasal infection and provoke a DTH response. These examples delineate a vital role for $T_H1$ CD4+ T lymphocytes in the control of primary viral infections and the development and maintenance of immunological memory.

There are several possible mechanisms for the protective function of $T_H1$ CD4+ T cells. IFNγ secretion has effects on a variety of cell types, including B cells, in which it influences switching of the IgG subclasses to IgG2a in mice (Arulanandam, et al., 2000, supra) and to IgG1 in humans (Bonifacio, et al., 1999, supra; Sousa, et al., 1998, supra; Hussain, et al., 1999, supra). These antibodies can enhance the efficiency of opsonization and complement fixation. Serum from neonatal mice given IL-12 prior to vaccination against influenza demonstrated heightened levels of influenza-specific, $T_H1$-dependent, IgG2a antibodies (Arulanandam, et al., 2000, supra). Passive transfer of serum from these mice to B cell deficient mice conferred better protection to live influenza challenge than serum from mice vaccinated without IL-12, which had mainly IgG1 influenza-specific antibodies. In other studies, however, the quantity of IgG antibody and not the subclass was important in conferring protection to viral challenge (Bachmann, et al., Science, 1997, 276:2024-2027). $TCR\beta^{-/-}$ $\delta^{-/-}$ mice infused with either $T_H1$ or $T_H2$ transgenic VSV-specific CD4$^+$ T cells elaborated polarized IgG antibodies to VSV, both of which conferred protective immunity (Maloy, et al., 2000, supra). Interestingly, we find that the human IgG1, $T_H1$-type antibody response to EBNA-1 is very large relative to other antibody responses (FIG. 11), consistent with the capacity of DCs to orchestrate strong antibody production from B cells (Fayette, et al., J. Exp. Med., 1997, 185:1909-1918; Dubois, et al., J. Exp. Med., 1997, 185:941-951).

$T_H1$ CD4$^+$ T cells could also control viral infections through cytotoxicity. In the current study, only $T_H1$ cells could lyse EBNA-1-expressing targets (FIG. 10). The restriction of cytotoxicity to $T_H1$ cells has been described previously (Bonifacio, et al., 1999, supra; Sousa, et al., 1998, supra; Hussain, et al., 1999, supra). Likewise, in a model in which ovalbumin-specific $T_H1$ and $T_H2$ cells were generated from TCR transgenic mice and tested for their ability to lyse murine tumor cells expressing ovalbumin, only the IFNγ-secreting CD4$^+$ T cells lysed tumor cells (Hussain, et al., 1999, supra).

Importantly, $T_H1$ and $T_H2$ cells differ in their ability to home to sites of infection (Austrup, et al., Nature, 1997, 385:81-83; O'Garra, et al., Curr. Biol., 1998, 8:R646-9). $T_H1$ cells but not $T_H2$ cells migrate in response to the corresponding chemokines (MCP-1, Mig and IP-10) that are produced in infected tissues (Maloy, et al., 2000, supra). This is due to differential expression of chemokine receptors, $T_H1$ cells expressing CCR2, CCR5 and CXCR3 and $T_H2$ cells, CCR4.

As mentioned above, in a murine model of tumor immunity, adoptive transfer of either $T_H1$ or $T_H2$ cells eradicated tumors, but only $T_H1$ cells generated immunological memory to tumor rechallenge (Hussain, et al., 1999, supra). Interestingly, the mechanisms of tumor eradication appeared very different between the two types of helper cells. In mice receiving $T_H1$ cells, the tumor was infiltrated mainly by lymphocytes. Conversely, the mice that received $T_H2$ cells demonstrated a tumor infiltrate marked by eosinophils and neutrophils.

Because the EBNA-1 protein is the sole EBV latency protein expressed in all forms of EBV-associated cancers and it elicits a $T_H1$ CD4$^+$ T cell response, this protein provides a new focus for vaccination, especially in children, and for immunotherapy for EBV-associated malignancies. Additionally, therapy targeted at polarizing EBNA-1-specific CD4$^+$ T lymphocytes towards $T_H1$ response would best involve targeting of EBNA-1 to immunogenic DCs.

The present invention is not to be limited in scope by the specific embodiments described herein. Indeed, various modifications of the invention in addition to those described herein will become apparent to those skilled in the art from the foregoing description and the accompanying Figures. Such modifications are intended to fall within the scope of the appended claims.

It is further to be understood that all values are approximate, and are provided for description.

All patents, patent applications, publications, and other materials cited herein are hereby incorporated herein reference in their entireties.

What is claimed is:

1. A method for making a human dendritic cell capable of eliciting an immune response to EBV-infected cells, which method comprises contacting a human dendritic cell with an isolated nucleic acid encoding an EBNA-1 polypeptide in humans; wherein the dendritic cell is capable of eliciting an immune response to an EBV-infected cell.

2. The method of claim 1, wherein the method comprises contacting the human dendritic cell with a vaccinia virus vector.

3. The method of claim 1, wherein the method comprises maturing the human dendritic cell in vitro.

4. The method of claim 3, wherein an immature human dendritic cell is matured by placing the immature dendritic cell in monocyte conditioned medium.

5. The method of claim 1, wherein the nucleic acid is RNA.

6. The method of claim 1, wherein the EBNA-1 polypeptide is a fusion protein of EBNA-1 and a heterologous amino acid sequence.

* * * * *